(12) United States Patent
Bramucci et al.

(10) Patent No.: US 7,034,140 B2
(45) Date of Patent: Apr. 25, 2006

(54) GENES INVOLVED IN ISOPRENOID COMPOUND PRODUCTION

(75) Inventors: Michael G. Bramucci, Folsom, PA (US); Patricia C. Brzostowicz, West Chester, PA (US); Qiong Cheng, Wilmington, DE (US); Kristy N Kostichka, Wilmington, DE (US); Pierre E. Rouviere, Wilmington, DE (US); Vasantha Nagarajan, Wilmington, DE (US); Luan Tao, Claymont, DE (US); Stuart M. Thomas, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 517 days.

(21) Appl. No.: 10/128,713

(22) Filed: Apr. 22, 2002

(65) Prior Publication Data

US 2003/0170847 A1    Sep. 11, 2003

Related U.S. Application Data

(60) Provisional application No. 60/285,910, filed on Apr. 24, 2001.

(51) Int. Cl.
*C12N 15/31*    (2006.01)
*C12N 15/63*    (2006.01)
*C12N 15/74*    (2006.01)
*C12N 15/82*    (2006.01)

(52) U.S. Cl. .................. 536/23.7; 536/23.1; 536/23.2; 435/183; 435/320.1; 435/419

(58) Field of Classification Search ............. 536/23.1, 536/23.2, 23.7; 435/183, 320.1, 419
See application file for complete search history.

(56) References Cited

U.S. PATENT DOCUMENTS 6,207,646 B1    3/2001    Krieg et al.

FOREIGN PATENT DOCUMENTS

EP        0157253 A1    3/1985

OTHER PUBLICATIONS

Querol J. et al. Biochemical and Biophysical Research Communications, 2001, vol. 289, pp. 155-160.*
Horbach et al., FEMS Microbiol. Lett. 111: 135-140, 1993.
Rohmer et al., Biochem. 295: 517-524, 1993.
Schwender et al., Biochem. 316: 73-80, 1996.
Eisenreich et al., Proc. Natl. Sci. USA 93: 6431-6436, 1996.
Cole et al., Nature, 393: 537-544, 1998.
White et al., Science, 286: 1571-1577, 1999.
Nelis and Leenheer, Appl. Bacteriol. 70:181-191, 1991.
Herz et al., 2000, Proc. NatL. Acad. Sci., 97: 2486.
Rohdich et al., 1999, Proc. Natl. Acad. Sci., 96: 11758.
Database GenBank, Accession No. Q10798, Mycrobacterium tuberculosis, Cole, S. T. et al., Oct. 6, 1996.
Kim et al., Metabolic Engineering of the Nonmevalonate-Isopentenyl Diphosphate Synthesis Pathway in *Escherichia coli* Enchances Lycopene Production, Biotechnol Bioeng. Feb. 20, 2001, vol. 72, No. 4, pp. 408-415.
Gordon-Kamm et al., Transformation of Maize Cells and Regeneration of Fertile Transgenic Plants, Jul. 1990, vol. 2, pp. 603-618.

* cited by examiner

*Primary Examiner*—Russell P. Kallis

(57) ABSTRACT

Genes have been isolated from *Rhodococcus erythropolis* AN12 strain encoding the isoprenoid biosynthetic pathway. The genes and gene products are the first isolated from a *Rhodococcus* strain. The genes and gene products of the present invention may be used in a variety of ways for the production of isoprenoid compounds in a variety of organisms.

8 Claims, 5 Drawing Sheets

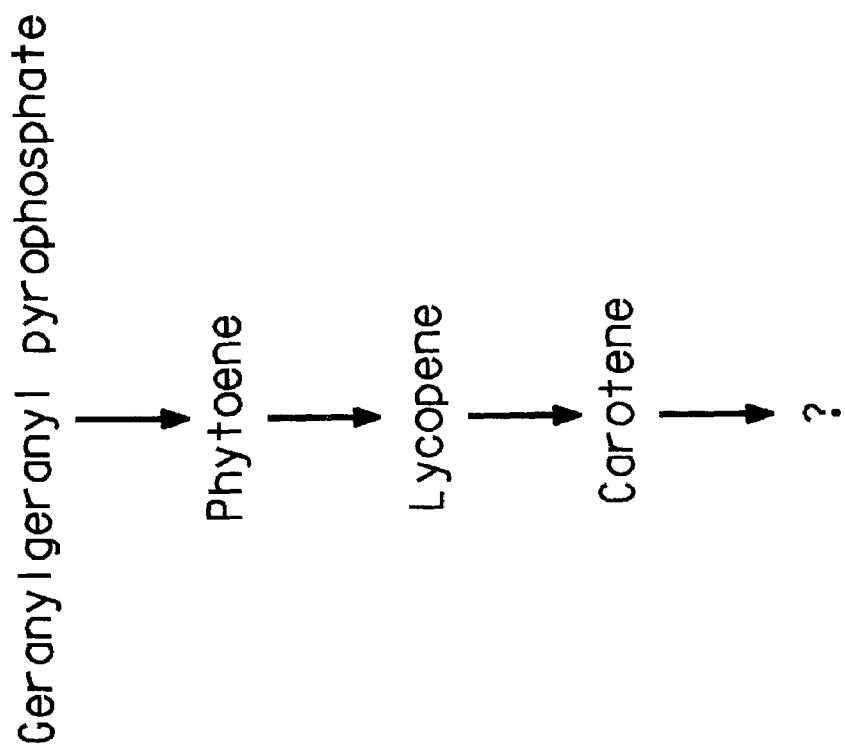

GENES INVOLVED IN ISOPRENOID COMPOUND PRODUCTION

This application claims priority to a provisional application No. 60/285,910 filed Apr. 24, 2001.

FIELD OF THE INVENTION

This invention is in the field of microbiology. More specifically, this invention pertains to nucleic acid fragments encoding enzymes useful for microbial production of isoprenoid compounds.

BACKGROUND OF THE INVENTION

Isoprenoids are an extremely large and diverse group of natural products that have a common biosynthetic origin, a single metabolic precursor, isopentenyl diphosphate (IPP). Isoprenoids includes all substances that are derived biosynthetically from the 5-carbon compound IPP (Spurgeon and Porter, Biosynthesis of Isoprenoid Compounds, pp 3–46, A Wiley-Interscience Publication (1981)). Some isoprenoids are also referred to as "terpenes" or "terpenoids". Isoprenoids are ubiquitous compounds found in all living organisms. Some of the well-known examples of isoprenoids are steroids (triterpenes), carotenoids (tetraterpenes), and squalene just to name a few.

For many years, it was accepted that IPP was synthesized through the well-known acetate/mevalonate pathway. However, recent studies have demonstrated that this mevalonate-dependent pathway does not operate in all living organisms. An alternate mevalonate-independent for IPP biosynthesis was initially characterized in bacteria and later in green algae and higher plant (Horbach et al., FEMS Microbiol. Lett. 111:135–140 (1993); Rohmer et al., Biochem. 295: 517–524 (1993); Schwender et al., Biochem. 316: 73–80 (1996); Eisenreich et al., Proc. Natl. Acad. Sci. USA 93: 6431–6436 (1996)).

Many steps in the mevalonate-independent isoprenoid pathway are known. For example, the initial steps involve the pyruvate and D-glyceraldehyde 3-Phosphate, to yield 5-carbon compound, D-1-deoxyxylulose-5-phosphate. A gene, dxs, that encodes D-1-deoxyxylulose-5-phosphate synthase (DXS) that catalyzes the synthesis of D-1-deoxyxylulose-5-phosphate was reported in Mycobacterium tuberculosis (Cole et al., Nature, 393:537–544,1998).

Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose- 5-phosphate reductoisomerase (DXR). The gene product of dxr that catalyzes the formation of 2-C-methyl-D-erythritol-4-phosphate has been reported in Mycobacterium tuberculosis (Cole et al., supra).

Steps converting 2-C-methyl-D-erythritol-4-phosphate to isopentenyl monophosphate are not well characterized although some steps are known. 2-C-methyl-D-erythritol-4-phosphate is converted into 4-diphosphocytidyl-2C-methyl-D-erythritol in a CTP dependent reaction by the enzyme encoded by the non-annotated gene ygbP. It has been reported that the YgbP protein is present in Mycobacterium tuberculosis, catalyzing the reaction mentioned above (Cole et al., Supra). Recently, ygbP gene was renamed as ispD as a part of isp gene cluster (SwissProt#Q46893) (Cole et al., Supra).

The $2^{nd}$ position hydroxy group of 4-diphosphocytidyl-2C-methyl-D-erythritol can be phosphorylated in an ATP dependent reaction by the enzyme encoded by ychB gene. The ychB gene product phosphorylates 4-diphosphocytidyl-2C-methyl-D-erythritol resulting in 4-diphosphocytidyl-2C-methyl-D-erythritol 2-phosphate. Cole et al. (Supra) have reported a YchB protein in Mycobacterium tuberculosis. Recently, ychB gene was renamed as ispE as a part of isp gene cluster (SwissProt#P24209) (Cole et al., Supra).

The product of the ygbB gene converts 4-diphosphocytidyl-2C-methyl-D-erythritol 2-phosphate to 2C-methyl-D-erythritol 2,4-cyclodiphosphate. Cole et al. (Supra) reported that ygbB gene product in Mycobacterium tuberculosis (Nature, 393:537–544, 1998). 2C-methyl-D-erythritol 2,4-cyclodiphosphate can be further converted into carotenoids through the carotenoid biosynthesis pathway. Recently, ygbB gene was renamed as ispF as a part of isp gene cluster (SwissProt#P36663). The reaction catalyzed by YgbP enzyme is carried out in CTP dependent manner. Isopentenyl monophosphate and isopentenyl diphosphate (IPP) are formed through a series of reactions not yet characterized but have recently been proposed to be mediated by LytB and GcpE (Cunningham et al., J. Bacteriol., 182:5841–5848, 2000; McAteer et al., J. Bacteriol., 183:7403–7407, 2000).

In E. coli, IPP can be converted to dimethylallyl diphosphate (DMAPP) by an isomerization reaction catalayzed by the idi gene which is dispensible, suggesting that DMAPP and IPP are produced independently (McAteer et al., J. Bacteriol., 183:7403–7407, 2000). There is a broad group of enzymes catalyzing the consecutive condensation of isopentenyl diphosphate (IPP) resulting in the formation of prenyl diphosphates of various chain lengths. Homologous genes of prenyl transferase have highly conserved regions in their amino acid sequences. They are heptaprenyl synthase, geranylgeranyl ($C_{20}$) diphosphate synthase (Cole et al., Supra), farnesyl ($C_{15}$) diphosphate synthase which can catalyze the synthesis of five prenyl diphosphates of various lengths.

Formation of $C_{40}$ phytoene is carried out by crtB gene that encodes phytoene synthase. Phytoene is formed by condensation of two molecules of $C_{20}$ precursor geranylgeranyl pyrophosphate (GGPP). Phytoene synthase has been isolated from Streptomyces coelicolor (GenBank#T36969).

Further down in the isoprenoid biosynthesis pathway, more genes are involved in synthesis of carotenoid. Pytoene desaturation step is carried out by crtI gene resulting in the formation of lycopene. A gene encoding phytoene dehydrogenase gene, crtI, has been isolated form Streptomyces coelicolor (GenBank#T36968).

Lycopene cyclization is carried out by crtY/L gene product, lycopene cyclase. Lycopene cyclase has been isolated from Deinococcus radiodurans (White et al. Science, 286: 1571–1577 (1999)).

Although many genes needed for isoprenoid and carotenoid synthesis synthesis have been characterized, the genes involved in the isoprenoid and/or carotenoid pathways in Rhodococcus bacteria are not described in the existing literature. There are many pigmented Rhodococcus bacteria which suggests that the ability to produce carotenoid pigments is widespread in these bacteria.

The problem to be solved therefore is to isolate the sequences responsible for isoprenoid biosynthesis in Rhodococcus for their eventual use in isoprenoid and carotenoid production. Applicants have solved the stated problem by isolating a nucleic acid fragment from a Rhodococcus erythropolis AN12 strain containing 10 open reading frames (ORFs) encoding enzymes involved in isoprenoid synthesis.

SUMMARY OF THE INVENTION

Ten open reading frames, each encoding enzymes in the isoprenoid biosynthetic pathway have been identified and isolated from *Rhodococcus erythropolis* AN12. The present enzymes are useful for the production of isoprenoids in recombinant organisms. These compounds are difficult and expensive to produce chemically and have potent antioxidant properties that are beneficial to human and animal health. *Rhodococcus* strains are good production hosts and are particularly suited to production of carotenoids due to inherent capacity to produce these compounds found in many species of the genus.

The present invention provides an isolated nucleic acid molecule selected from the group consisting of:
  (a) an isolated nucleic acid molecule encoding an isoprenoid biosynthetic enzyme having an amino acid sequence selected from the group consisting of SEQ ID NOs:2, 4, 6, 8, 10, 12, 14, 16, 18 and 20;
  (b) an isolated nucleic acid molecule encoding a isoprenoid biosynthetic enzyme that hybridizes with (a) under the following hybridization conditions: 0.1×SSC, 0.1% SDS, 65° C. and washed with 2×SSC, 0.1% SDS followed by 0.1×SSC, 0.1% SDS; or
  an isolated nucleic acid molecule that is complementary to (a), or (b).

Additionally the invention provides chimeric genes comprising the instant nucleic acid fragments operably linked to appropriate regulatory sequences and polypeptides encoded by the present nucleic acid fragments and chimeric genes.

The invention additionally provides transformed hosts comprising the instant nucleic acid sequences wherein the host cells are selected from the group consisting of bacteria, yeast, filamentous fungi, algae, and green plants.

In another embodiment the invention provides a method of obtaining a nucleic acid molecule encoding an isoprenoid compound biosynthetic enzyme comprising:
  (a) probing a genomic library with the nucleic acid molecule of any one of the present isolated nucleic acid sequences;
  (b) identifying a DNA clone that hybridizes with the nucleic acid molecule of any one of the present nucleic acid sequences; and
  (c) sequencing the genomic fragment that comprises the clone identified in step (b),
    wherein the sequenced genomic fragment encodes an isoprenoid biosynthetic enzyme.

Similarly the invention provides a method of obtaining a nucleic acid molecule encoding an isoprenoid biosynthetic enzyme comprising:
  (a) synthesizing an at least one oligonucleotide primer corresponding to a portion of the sequence selected from the group consisting of SEQ ID NOs:1, 3, 5, 7, 9, 11, 13, 15, 17 and 19; and
  (b) amplifying an insert present in a cloning vector using the oligonucleotide primer of step (a);

wherein the amplified insert encodes a portion of an amino acid sequence encoding an isoprenoid biosynthetic enzyme.

In another embodiment the invention provides a method for the production of isoprenoid compounds comprising: contacting a transformed host cell under suitable growth conditions with an effective amount of a fermentable carbon substrate whereby an isoprenoid compound is produced, said transformed host cell comprising a set of nucleic acid molecules encoding SEQ ID NOs:2, 4, 6, 8, 10, 12, 14, 16, 18 and 20 under the control of suitable regulatory sequences.

In an alternate embodiment the invention provides a method of regulating isoprenoid biosynthesis in an organism comprising, over-expressing at least one isoprenoid gene selected from the group consisting of SEQ ID NOs:1, 3, 5, 7, 9, 11, 13, 15, 17 and 19 in an organism such that the isoprenoid biosynthesis is altered in the organism. The regulation of isoprenoid biosynthesis may be accomplished by means of expressing genes on a multicopy plasmid, operably linking the relevant genes to regulated or inducible promoters, by antisense expression or by selective disruption of certain genes in the pathway.

Additionally a mutated gene is provided encoding a isoprenoid enzyme having an altered biological activity produced by a method comprising the steps of:
  (i) digesting a mixture of nucleotide sequences with restriction endonucleases wherein said mixture comprises:
    a) a native isoprenoid gene of the invention;
    b) a first population of nucleotide fragments which will hybridize to said native isoprenoid gene of the invention;
    c) a second population of nucleotide fragments which will not hybridize to said native isoprenoid gene of the invention; wherein a mixture of restriction fragments is produced;
  (ii) denaturing said mixture of restriction fragments;
  (iii) incubating the denatured said mixture of restriction fragments of step (ii) with a polymerase;
  (iv) repeating steps (ii) and (iii) wherein a mutated isoprenoid gene is produced encoding a protein having an altered biological activity.

BRIEF DESCRIPTION OF THE DRAWINGS AND SEQUENCE DESCRIPTIONS

Figure 1A:
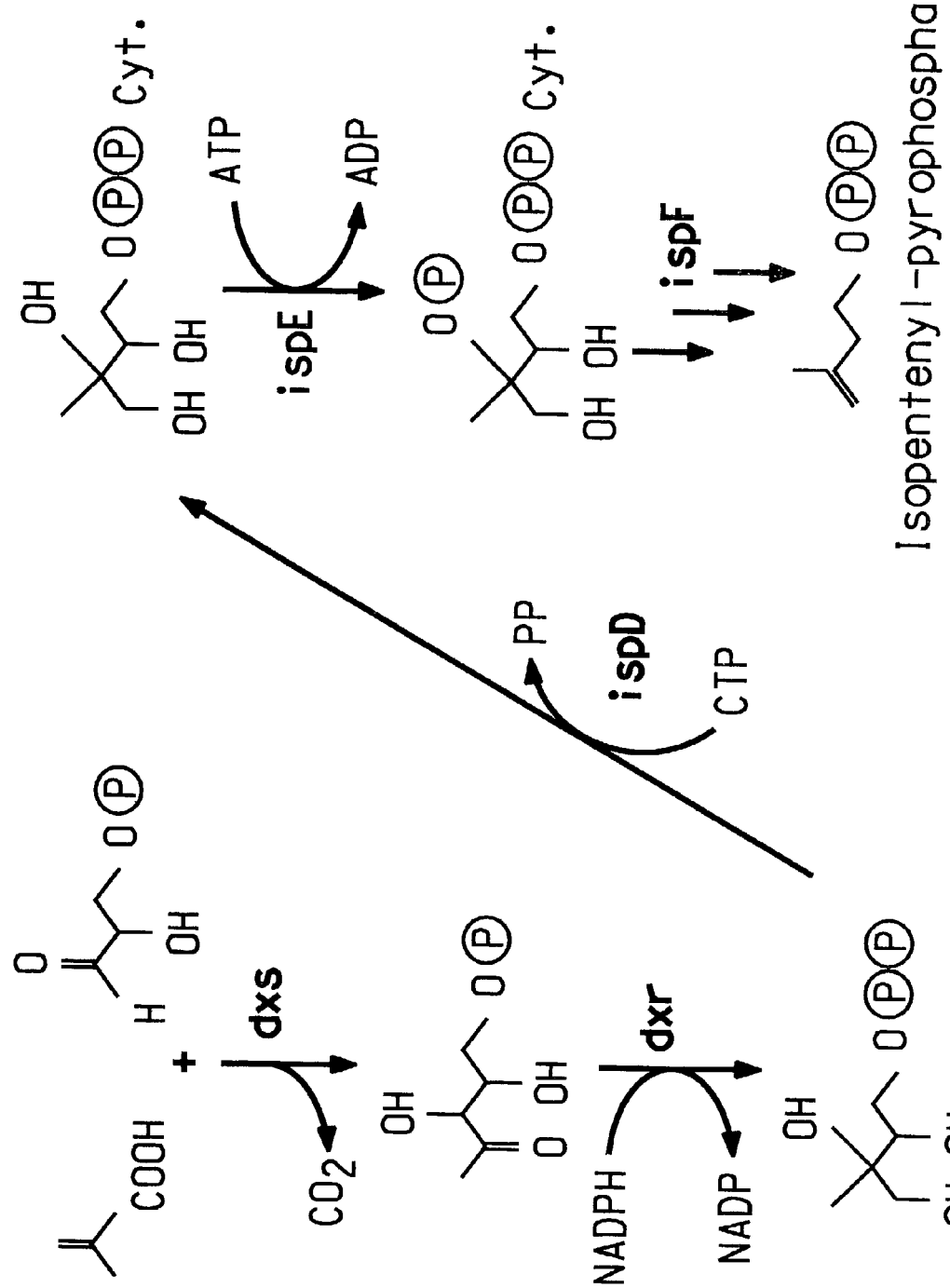
FIG. 1 shows the isoprenoid pathway and the putative function of the isoprenoid genes identified in AN12.

The invention can be more fully understood from the following detailed description and the accompanying sequence descriptions, which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of ORF 1 encoding dxs gene.

SEQ ID NO:2 is the deduced amino acid sequence of dxs encoded by ORF 1.

SEQ ID NO:3 is the nucleotide sequence of ORF 2 encoding dxr gene.

SEQ ID NO:4 is the deduced amino acid sequence of dxr encoded by ORF2.

SEQ ID NO:5 is the nucleotide sequence of ORF 3 encoding ygbP (ispD)gene.

SEQ ID NO:6 is the deduced amino acid sequence of ygbP (ispD)gene encoded by ORF 3.

SEQ ID NO:7 is the nucleotide sequence of ORF 4 encoding ychB (ispE) gene.

SEQ ID NO:8 is the deduced amino acid sequence of ychB (ispE) encoded by ORF 4.

SEQ ID NO:9 is the nucleotide sequence of ORF 5 encoding ygbB (ispF) gene.

SEQ ID NO:10 is the deduced amino acid sequence of ygbB (ispF)encoded by ORF 5.

SEQ ID NO:1 is the nucleotide sequence of ORF 6 encoding ispA gene.

SEQ ID NO:12 is the deduced amino acid sequence of ispA gene encoded by ORF 6.

SEQ ID NO:13 is the nucleotide sequence of ORF 7 encoding crtE gene.

SEQ ID NO:14 is the deduced amino acid sequence of crtE gene encoded by ORF 7.

SEQ ID NO:15 is the nucleotide sequence of ORF 8 encoding crtB gene.

SEQ ID NO:16 is the deduced amino acid sequence of crtB gene encoded by ORF8.

SEQ ID NO:17 is the nucleotide sequence of ORF 9 encoding crtI gene.

SEQ ID NO:18 is the deduced amino acid sequence of crtI gene encoded by ORF 9.

SEQ ID NO:19 is the nucleotide sequence of ORF 10 encoding crtL gene.

SEQ ID NO:20 is the deduced amino acid sequence of crtL gene encoded by ORF 10.

SEQ ID NOs:21–36 are the primer sequences.

DETAILED DESCRIPTION OF THE INVENTION

The present genes and their expression products are useful for the creation of recombinant organisms that have the ability to produce various isoprenoid compounds including carotenoid compounds. Nucleic acid fragments encoding the above mentioned enzymes have been isolated from a strain of *Rhodococcus erythropolis* and identified by comparison to public databases containing nucleotide and protein sequences using the BLAST and FASTA algorithms well known to those skilled in the art.

The genes and gene products of the present invention may be used in a variety of ways for the enhancement or manipulation of isoprenoid compounds.

The microbial isoprenoid pathway is naturally a multi-product platform for production of compounds such as carotenoids, quinones, squalene, and vitamins. These natural products may be from 5 carbon units to more than 55 carbon units in chain length. There is a general practical utility for microbial isoprenoid production for carotenoid compounds as these compounds are very difficult to make chemically (Nelis and Leenheer, *Appl. Bacteriol.* 70:181–191 (1991)). Most carotenoids have strong color and can be viewed as natural pigments or colorants. Furthermore, many carotenoids have potent antioxidant properties and thus inclusion of these compounds in the diet is thought to healthful. Well-known examples are β-carotene and astaxanthin.

In the case of *Rhodococcus erythropolis* the inherent capacity to produce carotenoids is particularly useful. Because *Rhodococcus* cells are resistant to many solvents and amenable to mixed phase process development, it is advantageous to use *Rhodococcus* strain as a production platform. *Rhodococcus* strains have been successfully used as a production hosts for the commercial production of other chemicals such as acrylamide.

The genes and gene sequences described herein enable one to incorporate the production of healthful carotenoids directly into the single cell protein product derived from *Rhodococcus erythropolis*. This aspect makes this strain or any bacterial strain into which these genes are incorporated a more desirable production host for animal feed due to the presence of carotenoids which are known to add desirable pigmentation and health benefits to the feed. Salmon and shrimp aquacultures are particularly useful applications for this invention as carotenoid pigmentation is critically important for the value of these organisms. (F. Shahidi, J. A. Brown, Carotenoid pigments in seafood and aquaculture Critical reviews in food Science 38(1): 1–67 (1998))

In addition to food supplements and feed additives the genes are useful for the production of carotenoids, and their derivatives, isoprenoid intermediates and their derivatives as pure products useful as pigments, steroids, flavors and fragrances and compounds with potential electro-optic applications.

In this disclosure, a number of terms and abbreviations are used. The following definitions are provided.

"Open reading frame" is abbreviated ORF.

"Polymerase chain reaction" is abbreviated PCR.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "isoprenoid" or "terpenoid" refers to the compounds are any molecule derived from the isoprenoid pathway including 10 carbon terpenoids and their derivatives, such as carotenoids and xanthophylls.

The term *Rhodococcus erythropolis* AN12 or AN12 refers to the *Rhodococcus erythropolis* AN12 strain and used interchangeably.

The term *Rhodococcus erythropolis* ATCC 47072 or ATCC 47072 refers to the *Rhodococcus erythropolis* ATCC 47072 strain and used interchangeably.

The term "Dxs" refers to 1-deoxyxylulose-5-phosphate synthase enzyme encoded by dxs gene represented in ORF 1.

The term "Dxr" refers to 1-deoxyxylulose-5-phosphate reductoisomerase enzyme encoded by dxr gene represented in ORF 2.

The term "YgbP" or "IspD" refers to 4-diphosphocytidyl-2C-methyl-D-erythritol synthase enzyme encoded by ygbP or ispD gene represented in ORF 3. The names of the gene, ygbP or ispD, are used interchangeably in this application. The names of gene product, YgbP or IspD are used interchangeably in this application.

The term "YchB" or "IspE" refers to isopentenyl monophosphate kinase enzyme encoded by ychB or ispE gene represented in ORF 4. The names of the gene, ychB or ispE, are used interchangeably in this application. The names of gene product, YchB or IspE are used interchangeably in this application.

The term "YgbB" or "IspF" refers to 2C-methyl-D-erythritol 2,4-cyclodiphosphate synthase enzyme encoded by ygbB or ispF gene represented in ORF 5. The names of the gene, ygbB or ispF, are used interchangeably in this application. The names of gene product, YgbB or IspF are used interchangeably in this application.

The term "IspA" refers to geranyltransferase or heptaprenyl diphosphate synthase enzyme as one of prenyl transferase family encoded by ispA gene represented in ORF 6.

The term "CrtE" refers to geranylgeranyl pyrophosphate synthase enzyme encoded by crtE gene represented in ORF 7.

The term "CrtB" refers to phytoene synthase enzyme encoded by crtB gene represented in ORF 8.

The term "CrtI" refers to phytoene dehydrogenase enzyme encoded by crtI gene represented in ORF 9.

The term "CrtL" refers to lycopene cyclase enzyme encoded by crtL gene represented in ORF 10.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2× SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Yet another set of preferred hybridization conditions includes hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I (Griffin, A. M., and Griffin, H. G., eds.) Humana Press, NJ (1994); Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID Nos. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992,111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, NY (1984); and by Ausubel, F. M. et al., *Current Protocols in Molecular Biology*, published by Greene Publishing Assoc. and Wiley-Interscience (1987).

A variety of nucleotide sequences have been isolated from *Rhodococcus erythropolis* AN12 strain encoding gene products involved in isoprenoid pathway. ORF's 1–5 for example encode enzymes early in isoprenoid pathway (FIG. 1) leading to IPP which is the precursor of all isoprenoid compounds. ORF 6 and 7 encode IspA and CrtE enzymes, respectively, that are involved in the elongation by condensing the IPP precursor. ORF's 8–10 are involved more specifically in carotenoid production.

Comparison of the dxs nucleotide base and deduced amino acid sequences (ORF 1) to public databases reveals that the most similar known sequences range from a distant as about 70% identical to the amino acid sequence of reported herein over length of 648 amino acid using a Smith-Waterman alignment algorithm (W. R. Pearson, *Camput. Methods Genome Res.*, [Proc. Int. Symp.] (1994), Meeting Date 1992, 111–20. Editor(s): Suhai, Sandor. Publisher Plenum, New York, N.Y.). Preferred amino acid fragments are at (east about 70%–80% identical to the sequences herein wherein 80%–90% identical is more preferred. Most preferred are amino acid fragments that are at least 95% identical to the amino acid fragments reported herein. Similarly, preferred Dxs encoding nucleic acid sequences corresponding to the instant ORF's are those encoding active proteins and which are at least 80% identical to the nucleic acid sequences of reported herein. More preferred Dxs nucleic acid fragments are at least 90% identical to the sequences herein. Most preferred are Dxs nucleic acid fragments that are at least 95% identical to the nucleic acid fragments reported herein.

Comparison of the Dxr base and deduced amino acid sequence to public databases reveals that the most similar known sequence is 71% identical at the amino acid level over a length of 385 amino acids (ORF 2) using a Smith-Waterman alignment algorithm (W. R. Pearson supra). Preferred amino acid fragments are at least about 70%–80% identical to the sequences herein wherein 80%–90% identical is more preferred. Most preferred are amino acid fragments that are at least 95% identical to the amino acid fragments reported herein. Similarly, preferred Dxr encoding nucleic acid sequences corresponding to the instant ORF are those encoding active proteins and which are at least 80% identical to the nucleic acid sequences of reported herein. More preferred Dxr nucleic acid fragments are at least 90% identical to the sequences herein. Most preferred are Dxr nucleic acid fragments that are at least 95% identical to the nucleic acid fragments reported herein.

Comparison of the YgbP (IspD) base and deduced amino acid sequences to public databases reveals that the most similar known sequences range from a distant as about 53% identical at the amino acid level over a length of 232 amino acids (ORF 3) using a Smith-Waterman alignment algorithm (W. R. Pearson supra). Preferred amino acid fragments are at least about 70%–80% identical to the sequences herein wherein 80%–90% identical is more preferred. Most preferred are amino acid fragments that are at least 95% identical to the amino acid fragments reported herein. Similarly, preferred YgbP (IspD) encoding nucleic acid sequences corresponding to the instant ORF are those encoding active proteins and which are at least 80% identical to the nucleic acid sequences of reported herein. More preferred YgbP (IspD) nucleic acid fragments are at least 90% identical to the sequences herein. Most preferred are YgbP (IspD) nucleic acid fragments that are at least 95% identical to the nucleic acid fragments reported herein.

Comparison of the YchB (IspE) base and deduced amino acid sequences to public databases reveals that the most similar known sequences range from a distant as about 62% identical at the amino acid level over a length of 311 amino acids (ORF 4) using a Smith-Waterman alignment algorithm (W. R. Pearson supra). Preferred amino acid fragments are at least about 70%–80% identical to the sequences herein wherein 80%–90% identical Is more preferred. Most preferred are amino acid fragments that are at least 95% identical to the amino acid fragments reported herein. Similarly, preferred YchB (IspE) encoding nucleic acid sequences corresponding to the instant ORF are those encoding active proteins and which are at least 80% identical to the nucleic acid sequences of reported herein. More preferred YchB (IspE) nucleic acid fragments are at least 90% identical to the sequences herein. Most preferred are YchB (IspE) nucleic acid fragments that are at least 95% identical to the nucleic acid fragments reported herein.

Comparison of the YgbB (IspE) base and deduced amino acid sequences to public databases reveals that the most similar known sequences range from a distant as about 57% identical at the amino acid level over a length of 158 amino acids (ORF 5) using a Smith-Waterman alignment algorithm (W. R. Pearson supra). Preferred amino acid fragments are at least about 70%–80% identical to the sequences herein wherein 80%–90% identical is more preferred. Most preferred are amino acid fragments that are at least 95% identical to the amino acid fragments reported herein. Similarly, preferred YgbB (IspF) encoding nucleic acid sequences corresponding to the instant ORF are those encoding active proteins and which are at least 80% identical to the nucleic acid sequences of reported herein. More preferred YgbB (IspF) nucleic acid fragments are at least 90% identical to the sequences herein. Most preferred are YgbB (IspF) nucleic acid fragments that are at least 95% identical to the nucleic acid fragments reported herein.

Comparison of the IspA base and deduced amino acid sequences to public databases reveals that the most similar known sequences range from a distant as about 57% identical at the amino acid level over a length of 344 amino acids (ORF 6) using a Smith-Waterman alignment algorithm (W. R. Pearson supra). Preferred amino acid fragments are at least about 70%–80% identical to the sequences herein wherein 80%–90% identical is more preferred. Most preferred are amino acid fragments that are at least 95% identical to the amino acid fragments reported herein. Similarly, preferred IspA encoding nucleic acid sequences corresponding to the instant ORF are those encoding active proteins and which are at least 80% identical to the nucleic acid sequences of reported herein. More preferred IspA nucleic acid fragments are at least 90% identical to the sequences herein. Most preferred are IspA nucleic acid fragments that are at least 95% identical to The nucleic acid fragments reported herein.

Comparison of the CrtE base and deduced amino acid sequences to public databases reveals that the most similar known sequences range from a distant as about 41% identical at the amino acid level over a length of 378 amino acids (ORF 7) using a Smith-Waterman alignment algorithm (W. R. Pearson supra). Preferred amino acid fragments are at least about 70%–80% identical to the sequences herein wherein 80%–90% identical is more preferred. Most preferred are amino acid fragments that are at least 95% identical to the amino acid fragments reported herein. Similarly, preferred CrtE encoding nucleic acid sequences corresponding to the instant ORF are those encoding active proteins and which are at least 80% identical to the nucleic acid sequences of reported herein. More preferred CrtE nucleic acid fragments are at least 90% identical to the sequences herein. Most preferred are CrtE nucleic acid fragments that are at least 95% identical to the nucleic acid fragments reported herein.

Comparison of the CrtB base and deduced amino acid sequences to public databases reveals that the most similar known sequences range from a distant as about 47% identical at the amino acid level over a length of 314 amino acids (ORF 8) using a Smith-Waterman alignment algorithm (W. R. Pearson supra). Preferred amino acid fragments are at least about 70%–80% identical to the sequences herein wherein 50%–90% identical is more preferred. Most preferred are amino acid fragments that are at least 95% identical to the amino acid fragments reported herein. Similarly, preferred nucleic acid sequences corresponding to the instant ORF are those encoding active proteins and which are at least 80% identical to the nucleic acid sequences of reported herein. More preferred nucleic acid fragments are at least 90% identical to the sequences herein. Most preferred are nucleic acid fragments that are at least 95% identical to the nucleic acid fragments reported herein.

Comparison of CrtI base and deduced amino acid sequences to public databases reveals that the most similar known sequences range from a distant as about 45% identical at the amino acid level over a length of 530 amino acids (ORE 9) using a Smith-Waterman alignment algorithm (W. R. Pearson supra). Preferred amino add fragments are at least about 70%–80% identical to the sequences herein wherein 80%–90% identical is more preferred. Most preferred are amino acid fragments that are at least 95% identical to the amino acid fragments reported herein. Similarly, preferred nucleic acid sequences corresponding to the instant ORF are those encoding active proteins and which are at least 80% identical to the nucleic acid sequences of reported herein. More preferred nucleic acid fragments are at least 90% identical to the sequences herein. Most preferred are nucleic acid fragments that are at least 95% identical to the nucleic acid fragments reported herein.

Comparison of CrtL base and deduced amino acid sequences to public databases reveals that the most similar known sequences range from a distant as about 31% identical at the amino acid level over a length of 376 amino acids (ORF 10) using a Smith-Waterman alignment algorithm (W. R. Pearson supra). Preferred amino acid fragments are at least about 70%–80% identical to the sequences herein wherein 80%–90% identical is more preferred. Most preferred are amino acid fragments that are at least 95% identical to the amino acid fragments reported herein. Similarly, preferred nucleic acid sequences corresponding to the instant ORF are those encoding active proteins and which are at least 80% identical to the nucleic acid sequences of reported herein. More preferred nucleic acid fragments are at least 90% identical to the sequences herein. Most preferred are nucleic acid fragments that are at least 95% identical to the nucleic acid fragments reported herein.

The nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor, S. et al., *Proc. Acad. Sci. USA* 82, 1074, (1985)) or strand displacement amplification (SDA, Walker, et al., *Proc. Natl. Acad. Sci. U.S.A.*, 89, 392, (1992)).

For example, genes encoding similar proteins or polypetides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A. *Adv. Immunol.* 36:1 (1984); Maniatis).

The genes and gene products of the instant sequences may be produced in heterologous host cells, particularly in the cells of microbial hosts. Expression in recombinant microbial hosts may be useful for the expression of various pathway intermediates; for the modulation of pathways already existing in the host for the synthesis of new products heretofore not possible using the host.

Preferred heterologous host cells for expression of the instant genes and nucleic acid fragments are microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid fragments. Because of transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include but are not limited to bacterial, fungal or yeast species such as *Aspergillus, Trichoderma, Saccharomyces, Pichia, Candida, Hansenula,* or bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Myxococcus, Thiobacillus, Methanobacterium* and *Klebsiella.*

Microbial expression systems and expression vectors containing regulatory sequences that direct high level expression of foreign proteins are well known to those skilled in the art. Any of these could be used to construct chimeric genes for production of the any of the gene products of the instant sequences. These chimeric genes could then be introduced into appropriate microorganisms via transformation to provide high level expression of the enzymes Accordingly it is expected, for example, that introduction of chimeric gene encoding the instant bacterial enzymes under the control of the appropriate promoters, will demonstrate increased isoprenoid production. It is contemplated that it will be useful to express the instant genes both in natural host cells as well as heterologous host. Introduction of the present genes into native host will result in elevated levels of existing isoprenoid production. Additionally, the instant genes may also be introduced into non-native host bacteria where there are advantages to manipulate the isoprenoid compound production that are not present in *Rhodococcus.*

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, ara, tet, trp, $IP_L$, $IP_R$, T7, tac, and trc (useful for expression in *Escherichia coli*) as well as the amy, apr, npr promoters and various phage promoters useful for expression in Bacillus.

Termination control regions may also be derived from various genes native to the preferred hosts. Optionally, a termination site may be unnecessary, however, it is most preferred if included.

Knowledge of the sequence of the present genes will be useful in manipulating the isoprenoid biosynthetic pathways in any organism having such a pathway and particularly in methanotrophs. Methods of manipulating genetic pathways are common and well known in the art. Selected genes in a particularly pathway may be upregulated or down regulated by variety of methods. Additionally, competing pathways organism may be eliminated or sublimated by gene disruption and similar techniques.

Once a key genetic pathway has been identified and sequenced specific genes may be upregulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Alternatively it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods for gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al. (1989) *J. Bacteriol.* 171:4617–4622, Balbas et al. (1993) *Gene* 136:211–213, Gueldener et al. (1996) *Nucleic Acids Res.* 24:2519–2524, and Smith et al. (1996) *Methods Mol. Cell. Biol.* 5:270–277.)

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992).

Another non-specific method of gene disruption is the use of transposoable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

Within the context of the present invention it may be useful to modulate the expression of the identified isoprenoid pathway by any one of the above described methods. For example, the present invention provides a number of genes encoding key enzymes in the terpenoid pathway leading to the production of pigments and smaller isoprenoid compounds. The isolated genes include the dxs and dxr genes, the ispA, D, E, and F genes, the crtE, B, I, and L genes. In particular it may be useful to up-regulate the initial condensation of 3-carbons (pyruvate and C1 aldehyde group, D-glyceraldehyde 3-Phosphate), to yield 5-carbon compound (D-1-deoxyxylulose-5-phosphate) mediated by the dxs gene. Alternatively, if it is desired to produce a specific non-pigment isoprenoid, it may be desirable to disrupt various genes at the downstream end of the pathway. For example, crtl gene that is known to encode phytoene dehydrogenase that is a part of carotenoid biosynthesis pathway. It may be desirable to use gene disruption or antisense inhibition of this gene if a smaller, upstream terpenoid is the desired product of the pathway.

Where commercial production of the iosprenoid products of the present genes are desired a variety of culture methodologies may be applied. For example, large-scale production of a specific gene product, overexpressed from a recombinant microbial host may be produced by both Batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of the products of the present genes may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, methane or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of Candida will metabolize alanine or oleic acid (Sulter et al., *Arch. Microbiol.* 153:485–489 (1990)). Hence it is contemplated that the source of carbon utilized in the present invention may encompass a wide variety of carbon containing substrates and will only be limited by the choice of organism.

Plants and algae are also known to produce isoprenoid compounds. The nucleic acid fragments of the instant invention may be used to create transgenic plants having the ability to express the microbial protein. Preferred plant hosts will be any variety that will support a high production level of the instant proteins. Suitable green plants will include but are not limited to soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum sp*), barley (*Hordeum vulgare*), oats (*Avena sativa, L*), sorghum (*Sorghum bicolor*), rice (*Oryza sativa*), *Arabidopsis*, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include but not limited to commercially significant hosts such as *Spirulina, Haemotacoccus*, and *Dunalliela*. Overexpression of the isoprenoid compounds may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequences or the present invention should be capable of promoting expression of the present gene product. High level plant promoters that may be used in this invention include the promoter of the small subunit (ss) of the ribulose-1,5-bisphosphate carboxylase from example from soybean (Berry-Lowe et al., *J. Molecular and App. Gen.*, 1:483–498 1982)), and the promoter of the chlorophyll a/b binding protein. These two promoters are known to be light-induced in plant cells (see, for example, *Genetic Engineering of Plants, an Agricultural Perspective*, A. Cashmore, Plenum, N.Y. (1983), pages 29–38; Coruzzi, G. et al., *The Journal of Biological Chemistry*,258:1399 (1983), and Dunsmuir, P. et al., *Journal of Molecular and Applied Genetics*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA blots (Southern, *J. Mol. Biol.* 98, 503, (1975)). Northern analysis of mRNA expression (Kroczek, *J. Chromatogr. Biomed. Appl.*, 618 (1–2) (1993) 133–145), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol. Biol.* 42:21–53 (1991)), or nuclear localization signals (Raikhel, *N. Plant Phys.* 100: 1627–1632 (1992)) added and/or with targeting sequences that are already present removed. While the references cited give examples of each of these, the list is not exhaustive and more targeting signals of utility may be discovered in the future that are useful in the invention.

It is contemplated that the present nucleotides may be used to produce gene products having enhanced or altered activity. Various methods are known for mutating a native gene sequence to produce a gene product with altered or enhanced activity including but not limited to error prone PCR (Melnikov et al., *Nucleic Acids Research*, (Feb. 15, 1999) Vol. 27, No. 4, pp. 1056–1062); site directed mutagenesis (Coombs et al., *Proteins* (1998), 259–311, 1 plate. Editor(s): Angeletti, Ruth Hogue. Publisher: Academic, San Diego, Calif.) and "gene shuffling" (U.S. Pat. Nos. 5,605, 793; 5,811,238; 5,830,721; and 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double stranded and can be of various lengths ranging form 50 bp to 10 kb. The sequences may be randomly digested into fragments ranging from about 10 bp to 1000 bp, using restriction endonucleases well known in the art (Maniatis supra). In addition to the instant microbial sequences, populations of fragments that are hybridizable to all or portions of the microbial sequence may be added. Similarly, a population of fragments which are not hybridizable to the instant sequence may also be added. Typically these additional fragment populations are added in about a 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTP's (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocol. (Manatis supra).

Furthermore, a hybrid protein can be assembled by fusion of functional domains using the gene shuffling (exon shuffling) method (Nixon et al., PNAS, 94:1069–1073 (1997)). The functional domain of the instant gene can be combined with the functional domain of other genes to create novel enzymes with desired catalytic function. A hybrid enzyme may be constructed using PCR overlap extension method and cloned into the various expression vectors using the techniques well known to those skilled in art.

Description of the Preferred Embodiments

The original environmental sample containing *Rhodococcus erythropolis* AN12 strain was obtained from wastewater treatment facility. One ml of activated sludge was inoculated directly into 10 ml of S12 medium. Aniline was used as the sole source of carbon and energy. The culture was maintained by addition of 100 ppm aniline every 2–3 days. The culture was diluted (1:100 dilution) every 14 days. Bacteria that utilize aniline as a sole source of carbon and energy were further isolated and purified on S12 agar. Aniline (5 µL) was placed on the interior of each culture dish lid.

When 16s rRNA gene of AN12 was sequenced and compared to other 16s rRNA sequence in the GenBank sequence database, 16s rRNA gene of AN12 strain has at least 98% similarity to the 16s rRNA gene sequences of high G+C gram positive Rhodococcus genus.

Figure 1B:
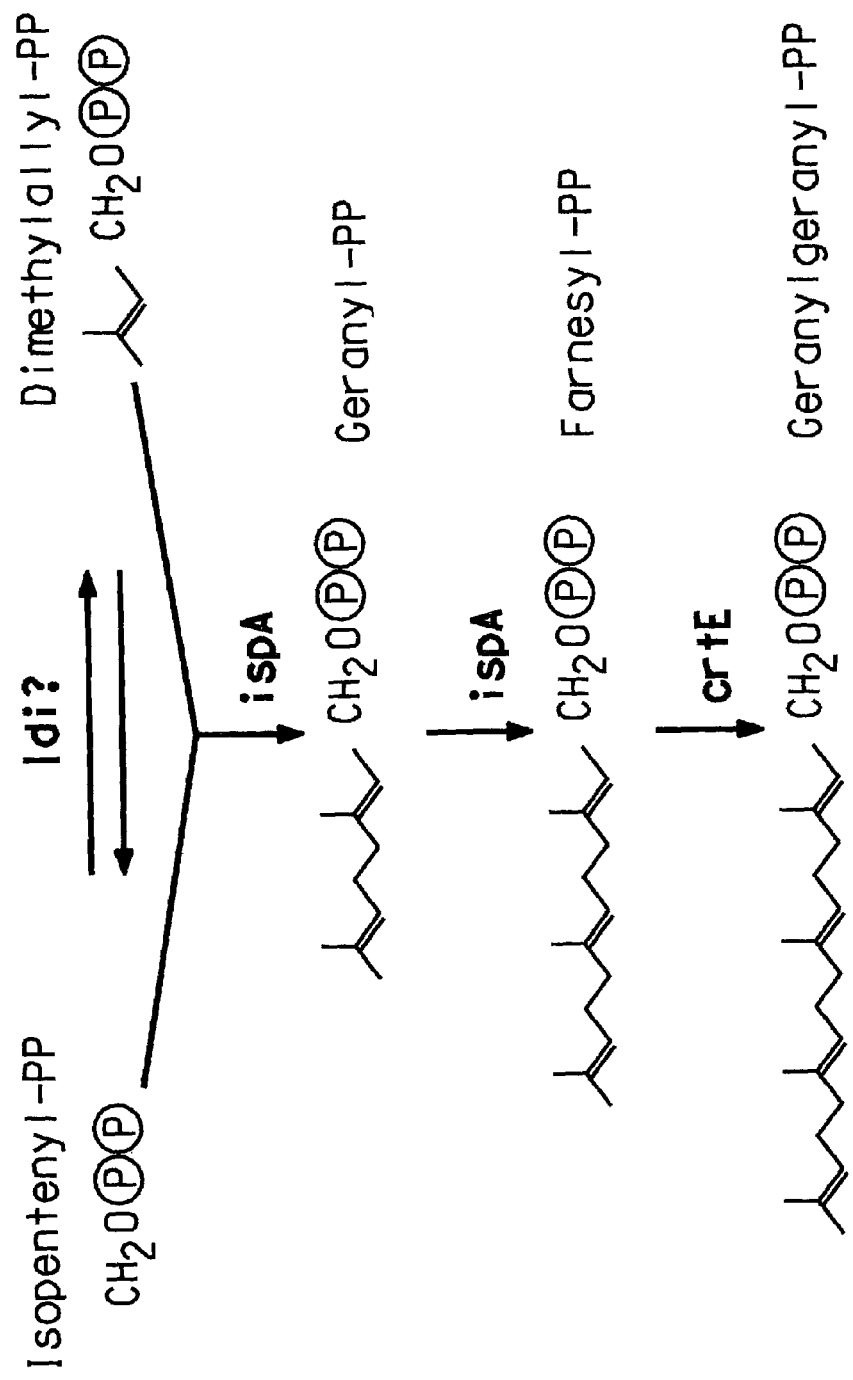

Table 1 summarizes the 10 genes identified by genome sequencing from *Rhodococcus erythropolis* strain AN12 which are involved in the isoprenoid pathway for carotenoids synthesis. The biochemical pathway for carotenoids synthesis and the putative assignment of the gene function is shown in FIG. 1.

Figure 2:
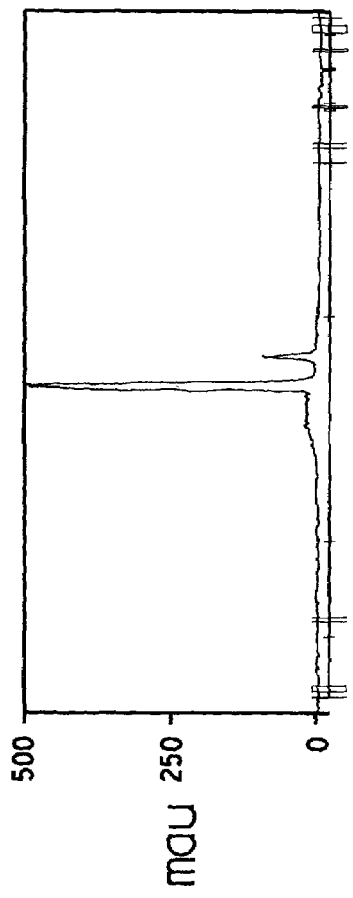
FIG. 2 shows HPLC analysis of carotenoid pigments from *Rhodococcus erythropolis* AN 12 strain and ATCC 47072.
Figure 2:
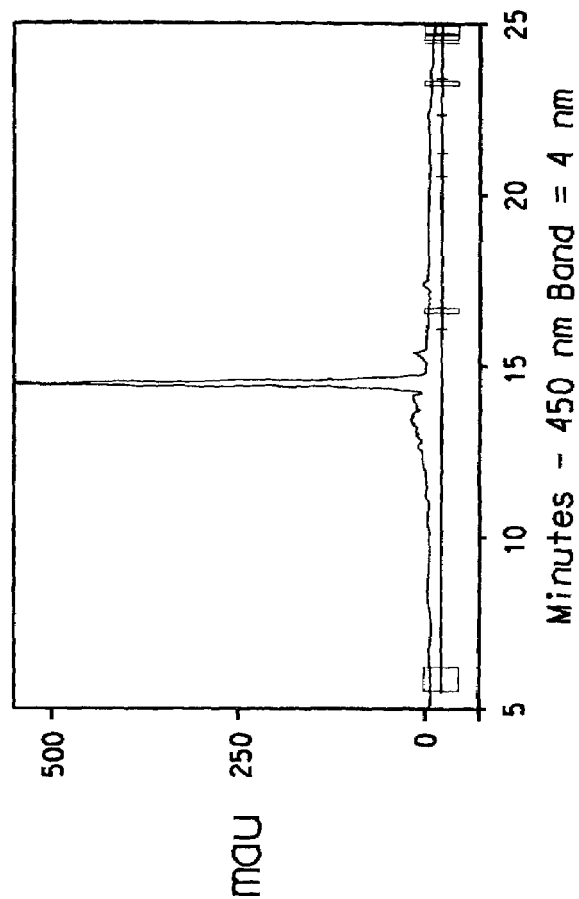

*Rhodoccocus erythropolis* AN12 is naturally pigmented. The pigment of AN12 was extracted and compared to the carotenoid pigment of *Rhodococcus erythropolis* strain ATCC 47072. Pigments from both strains were extracted into acetone, dried under nitrogen, and re-dissolved in methanol. Soluble materials from both strains were analyzed by HPLC. The pigment from AN12 showed a similar profile as the carotenoid pigment from ATCC 47072 strain in HPLC analysis (FIG. 2). The molecular weight of the major pigment in ATCC 47072 strain was determined to be 550 dalton by MALDI-MS analysis and LC-MS.

The dxs gene encodes the 1-deoxyxylulose-5-phosphate synthase that catalyzes the first step of the synthesis of 1-deoxyxylulose-5-phosphate from glyceraldehyde-3-phosphate and pyruvate precursors in the isoprenoid pathway. When dxs genes with different DNA lengths of upstream promoter regions from AN12 were cloned into the multicopy shuttle vector, electroporated into ATCC 47072 host, and overexpressed, transformed colonies appeared darker than the colonies with vector control. Carotenoid production in the transformed colonies was evaluated spectrophotometrically and using HPLC. Increased carotenoid production was observed in transformed colonies (Table 2).

The activity of the present genes and gene products has been confirmed by a study showing the loss of carotenoid production in ATCC 47072 strain when the gene was disrupted by homologous recombination. Targeted genes were crtE and crtI. Truncated portions of crtE and crtI genes from ATCC 47072 strain were amplified using PCR. The primer sequences for PCR were based on AN12 sequence. The amplified fragments of crtE and crtI genes had about 95% identity on the DNA level to the respective genes from AN12 strain. The crtE fragment and the crtI fragment were first cloned into pCR2.1 TOPO vector (Invitrogen, Carlsbad, Calif.). The TOPO clones were digested with NcoI and the crtE or crtI fragments were subsequently cloned into the NcoI site of pBR328. The resulted constructs were confirmed by sequencing and designated as pDCQ100 for the crtE clone and pDCQ101 for the crtI clone. Approximately one µg DNA of pDCQ100 and pDCQ101 were introduced into Rhodococcus ATCC 47072 by electroporation and plated on NBYE plates with 10 µg/ml tetracycline. The pBR328 vector does not replicate in Rhodococcus. The tetracycline resistant transformants obtained after 3–4 days of incubation at 30° C. were generated by chromosomal integration. Integration into the targeted crtE or crtI gene on chromosome of ATCC 47072 was confirmed by PCR. The vector specific primers paired with the gene specific primers were used for PCR using chromosomal DNA prepared from the tetracycline resistant transformants as the templates. PCR fragments of the expected sizes were amplified from the tetracycline resistant transformants, but no PCR product was obtained from the wild type ATCC 47072. When the two gene specific primers were used, no PCR fragment was obtained with the tetracycline resistant transformant due to the insertion of the large vector DNA. The PCR fragments obtained with the vector specific primers and the gene specific primers were sequenced. Sequence analysis of the junction of the vector and the crtE or crtI gene confirmed that the single crossover recombination occurred at the expected sites and disrupted the target genes crtE or crtI.

The phenotypes of the CrtE and CrtI disruption mutants of ATCC 47072 were analyzed. Colonies of CrtE or CrtI disruption mutants were pale white. It appeared that the pigments present in the wild type strain were lost in both mutants. HPLC analysis of the carotenoids of the mutants confirmed the visual inspection result.

The CrtI disruption mutant did not have the two HPLC peaks present in the wild type strains when monitored at 450 nm. (Table 3) These results confirmed the role of CrtI protein in carotenoids biosynthesis. Knockout of the crtI gene resulted in no carotenoid pigment as represented by the two HPLC peaks at 450 nm. Phytoene (colorless) accumulation in the CrtI disruption mutant confirms the function of CrtI protein as the phytoene dehydogenase as suggested by the BLAST search.

The CrtE disruption mutant had neither the two HPLC peaks present in the wild type nor the phytoene peak in the CrtI disruption mutant. These results also confirmed the role of CrtE protein in carotenoids biosynthesis. No phytoene accumulation in CrtE disruption mutant was consistent with the function of CrtE protein as geranylgeranyl pyrophosphate synthase, which acts prior to the phytoene synthesis step in the pathway.

The lycopene cyclase (ORF 10) identified in Rhodococcus erythropolis strain AN12 showed high sequence similarity to the CrtL-type of lycopene cyclases in plants and cyanobacterium (Table 1). The tri-alkyl amine compounds, 2-(4-methylphenoxy)-triethylamine hydrochloride (MPTA) and 2-(4-chlorophenylthio)-triethylamine hydrochloride (CPTA), have been shown to specifically inhibit the CrtL-type of lycopene cyclases and not the non-photosynthetic bacterial CrtY-type of lycopene cyclases (Cunningham, Jr., et al, Molecular structure and enzymatic function of lycopene cyclase from the Cyanobacterium Synechococcus sp. strain PCC7942, The *Plant Cell,* 1994, Vol.6:1107). The effect of MPTA or CPTA on carotenoid production in *Rhodococcus erythropolis* (ATCC 47072 strain) was examined. In the presence of 40 µM of MPTA or CPTA, carotenoid production was significantly decreased using lycopene as a substrate.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology,* Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "ml" means milliliters, "L" means liters.

Example 1

Isolation and Characterization of Strain AN12

Example 1 describes the isolation of strain AN12 of *Rhodococcus erythropolis* on the basis of being able to grow on aniline as the sole source of carbon and energy. Analysis of a 16S rRNA gene sequence indicated that strain AN12 was related to high G+C Gram positive bacteria belonging to the genus *Rhodococcus*.

Bacteria that grew on aniline were isolated from an enrichment culture. The enrichment culture was established by inoculating 1 ml of activated sludge into 10 ml of S12 medium (10 mM ammonium sulfate, 50 mM potassium phosphate buffer (pH 7.0), 2 mM $MgCl_2$, 0.7 mM $CaCl_2$, 50 µM $MnCl_2$, 1 µM $FeCl_3$, 1 µM $ZnCl_3$, 1.72 µM $CuSO_4$, 2.53 µM $CoCl_2$, 2.42 µM $Na_2MoO_2$, and 0.0001% $FeSO_4$) in a 125 ml screw cap Erlenmeyer flask. The activated sludge was obtained from a wastewater treatment facility. The enrichment culture was supplemented with 100 ppm aniline added directly to the culture medium and was incubated at 25° C. with reciprocal shaking. The enrichment culture was maintained by adding 100 ppm of aniline every 2–3 days. The culture was diluted every 14 days by replacing 9.9 ml of the culture with the same volume of S12 medium. Bacteria that utilized aniline as a sole source of carbon and energy were isolated by spreading samples of the enrichment culture onto S12 agar. Aniline (5 µL) was placed on the interior of each petri dish lid. The petri dishes were sealed with parafilm and incubated upside down at room temperature (approximately 25° C.). Representative bacterial colonies were then tested for the ability to use aniline as a sole source of carbon and energy. Colonies were transferred from the original S12 agar plates used for initial isolation to new S12 agar plates and supplied with aniline on the interior of each petri dish lid. The petri dishes were sealed with parafilm and incubated upside down at room temperature (approximately 25° C.).

The 16S rRNA genes of each isolate were amplified by PCR and analyzed as follows. Each isolate was grown on R2A agar (Difco Laboratories, Bedford, Mass.). Several colonies from a culture plate were suspended in 100 µl of water. The mixture was frozen and then thawed once. The 16S rRNA gene sequences were amplified by PCR using a commercial kit according to the manufacturer's instructions (Perkin Elmer) with primers HK12 (5'-GAGTTTGATC-CTGGCTCAG-3') (SEQ ID NO:21) and HK13 (5'-TACCT-TGTTACGACTT-3') (SEQ ID NO:22). PCR was performed in a Perkin Elmer GeneAmp 9600 (Norwalk, Conn.). The samples were incubated for 5 min at 94° C. and then cycled 35 times at 94° C. for 30 sec, 55° C. for 1 min, and 72° C. for 1 min. The amplified 16S rRNA genes were purified using a commercial kit according to the manufacturer's instructions (QIAquick PCR Purification Kit, Qiagen, Valencia, Calif.) and sequenced on an automated ABI sequencer. The sequencing reactions were initiated with primers HK12, HK13, and HK14 (5'-GTGCCAG-CAGYMGCGGT-3') (SEQ ID NO:23, where Y=C or T, M=A or C). The 16S rRNA gene sequence of each isolate was used as the query sequence for a BLAST search [Altschul, et al., *Nucleic Acids Res.* 25:3389–3402(1997)] of GenBank for similar sequences.

A 16S rRNA gene of strain AN12 was sequenced and compared to other 16S rRNA sequences in the GenBank sequence database. The 16S rRNA gene sequence from strain AN12 was about 98% similar to the 16S rRNA gene sequences of high G+C Gram positive bacteria belonging to the genus *Rhodococcus*.

Example 2

Preparation of AN12 Genomic DNA for Sequencing and Sequence Generation

Genomic DNA preparation. *Rhodococcus erythropolis* AN12 was grown in 25 mL NBYE medium (0.8% nutrient broth, 0.5% yeast extract, 0.05% Tween 80) till mid-log phase at 37° C. with aeration. Bacterial cells were centrifuged at 4,000 g for 30 min at 4° C. The cell pellet was washed once with 20 ml 50 mM $Na_2CO_3$ containing 1M KCl (pH 10) and then with 20 ml 50 mM NaOAc (pH 5). The cell pellet was gently resuspended in 5 ml of 50 mM Tris-10 mM EDTA (pH 8) and lysozyme was added to a final concentration of 2 mg/mL. The suspension was incubated at 37° C. for 2 h. Sodium dodecyl sulfate was then added to a final concentration of 1% and proteinase K was added to 100 µg/ml final concentration. The suspension was incubated at 55° C. for 5 h. The suspension became clear and the clear lysate was extracted with equal volume of phenol:chloroform:isoamyl alcohol (25:24:1). After centrifuging at 17,000 g for 20 min, the aqueous phase was carefully removed and transferred to a new tube. Two volumes of ethanol were added and the DNA was gently spooled with a sealed glass pasteur pipet. The DNA was dipped into a tube containing 70% ethanol, then air dried. After air drying, DNA was resuspended in 400 µl of TE (10 mM Tris-1 mM EDTA, pH 8) with RNaseA (100 µg/mL) and stored at 4° C.

Library construction. 200 to 500 µg of chromosomal DNA was resuspended in a solution of 300 mM sodium acetate, 10 mM Tris-HCl, 1 mM Na-EDTA, and 30% glycerol, and sheared at 12 psi for 60 sec in an Aeromist Downdraft Nebulizer chamber (IBI Medical products, Chicago, Ill.). The DNA was precipitated, resuspended and treated with Bal31 nuclease (New England Biolabs, Beverly, Mass.). After size fractionation by 0.8% agarose gel electrophoresis, a fraction (2.0 kb, or 5.0 kb) was excised, cleaned and a two-step ligation procedure was used to produce a high titer library with greater than 99% single inserts.

Sequencing. A shotgun sequencing strategy approach was adopted for the sequencing of the whole microbial genome (Fleischmann, Robert et al., Whole-Genome Random sequencing and assembly of *Haemophilus influenzae* Rd *Science*, 269:1995).

Sequence was generated on an ABI Automatic sequencer using dye terminator technology (U.S. Pat. No. 5,366,860; EP 272007) using a combination of vector and insert-specific primers. Sequence editing was performed in either DNAStar (DNA Star Inc., Madison, Wis.) or the Wisconsin GCG program (Wisconsin Package Version 9.0, Genetics Computer Group (GCG), Madison, Wis.) and the CONSED package (version 7.0). All sequences represent coverage at least two times in both directions.

Example 3

Identification of ORFs in the Isoprenoid Pathway from Strain AN12

ORFs 1–10 were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant (nr) GenBank CDS translations, sequences derived from the 3-dimensional structure Brookhaven Protein Data Bank, the SWISS-PROT protein sequence database, EMBL, and DDBJ databases). The sequences obtained in Example 2 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Altschul, S. F., et al., *Nucleic Acid Res.* 25:3389–3402) (1997) provided by the NCBI. The results of the BLAST comparison is given in Table 1 which summarize the sequences to which they have the most similarities. Table 1 displays data based on the BLAST algorithm with values reported in expect values. The Expect value estimates the statistical significance of the match, specifying the number of matches, with a given score, that are expected in a search of a database of this size absolutely by chance.

protein with homology to ORF 3 was later identified as a homolog of ygbP (ispD) encoding 4-diphosphocytidyl-2C-methyl-D-erythritol synthase (Rohdich, et al, 1999, PNAS 96:11758). The downstream gene Rv3581c encoding the protein with homology to ORF 5 was later identified as a homolog of ygbB (ispF) encoding 2C-methyl-D-erythritol 2,4-cyclodiphosphate synthase (Herz, et al, 2000, PNAS 97:2486). The ORF 3 and ORF 5 are also closely adjacent on the chromosome of *Rhodococcus* strain AN12 with the same organization as the ygbP and ygbB homologs in *M. tuberculosis, E. coli, H. influenzae* and *B. subtilis* (Rohdich, et al, 1999, PNAS 96:11758). Two other genes crtE (ORF7) and crtI (ORF9) are also linked on AN12 chromosome.

ORF 10 had homology to (β-lycopene cyclases.that add β-cyclic groups to the ends of the lycopene substrate. There

TABLE 1

Genes involved in isoprenoid pathway from *Rhodococcus erythropolis* AN12.

| ORF | Gene | Similarity Identified | % Identity[a] | % Similarity[b] | E-value[c] | Citation |
|---|---|---|---|---|---|---|
| 1 | dxs | sp\|O07184\|DXS_MYCTU<br>1-deoxyxylulose-5-phosphate synthase<br>[*Mycobacterium tuberculosis*] | 70 | 83 | 0 | Cole S. T. et al<br>Nature 393 (6685), 537–544<br>(1998) |
| 2 | dxr | sp\|Q10798\|DXR_MYCTU<br>1-deoxy-d-xylulose 5-phosphate<br>reductoisomerase<br>[*Mycobacterium tuberculosis*] | 71 | 79 | e–148 | Cole S. T. et al<br>Nature 393 (6685), 537–544<br>(1998) |
| 3 | ispD/<br>ygbP | sp\|P96864\|YZ82_MYCTU<br>4-diphosphocytidyl-2-C-methylerythritol synthase<br>[*Mycobacterium tuberculosis*] | 53 | 66 | 2e–54 | Cole S. T. et al<br>Nature 393 (6685), 537–544<br>(1998) |
| 4 | ispE/<br>ychB | sp\|O05596\|IPK_MYCTU<br>Isopentenyl monophosphate kinase<br>[*Mycobacterium tuberculosis*] | 62 | 74 | 2e–99 | Cole S. T. et al<br>Nature 393 (6685), 537–544<br>(1998) |
| 5 | ispF/<br>ygbB | sp\|P96863\|YZ81_MYCTU<br>2C-methyl-D-erythritol 2,4-cyclodiphosphate<br>synthase.<br>[*Mycobacterium tuberculosis*] | 57 | 64 | 6e–41 | Cole S. T. et al<br>Nature 393 (6685), 537–544<br>(1998) |
| 6 | ispA | pir\|E70549<br>Heptaprenyl diphosphate synthase<br>[*Mycobacterium tuberculosis*] | 57 | 66 | 2e–99 | Cole S. T. et al<br>Nature 393 (6685), 537–544<br>(1998) |
| 7 | crtE | pir\|G70935<br>idsA2 protein (GGPP synthase)<br>[*Mycobacterium tuberculosis*] | 41 | 55 | e–67 | Cole S. T. et al<br>Nature 393 (6685), 537–544<br>(1998) |
| 8 | crtB | pir\|T36969<br>Phytoene synthase<br>[*Streptomyces coelicolor*] | 47 | 56 | 8e–64 | Seeger K. J. et al<br>Unpublished |
| 9 | crtI | pir\|T36968<br>Putative phytoene dehydrogenase<br>[*Streptomyces coelicolor*] | 45 | 56 | e–113 | Seeger K. J. et al<br>Unpublished |
| 10 | crtL | sp\|Q9RW68\|Y801_DEIRA<br>Lycopene cyclase<br>[*Deinococcus radiodurans*] | 31 | 45 | 2e–37 | White O. et al<br>Science 286 (5444), 1571–1577<br>(1999) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that is expected in a search of a database of this size absolutely by chance.

Table 1 summarizes the ten genes we identified by genome sequencing from *Rhodococcus erythropolis* strain AN12 which are involved in the isoprenoid pathway for carotenoids synthesis. The biochemical pathway for carotenoids synthesis and the putative assignment of the gene function is shown in FIG. 1.

The top hits from the BLAST search for ORF3 and ORF5 were originally annotated as hypothetical proteins from *Mycobacterium tuberculosis*. The genes encoding these two hypothetical proteins were linked in the Mycobacterium chromosome. The upstream gene Rv3582c encoding the are two classes of β-lycopene cyclases that are functionally very similar, the crtL-type of cyclases from cyanobacterium and plants, and the crtY-type of cyclases from other bacteria. Despite the functional similarity, these two classes of cyclases shared limited structural similarities. ORF 10 showed highest similarity to lycopene cyclase from *Deinococcus radiodurans*. The lycopene cyclases from *Rhodococcus erythropolis* strain AN12 and *Deinococcus radiodurans* strain R1all showed higher homology to plant crtL-b type of lycopene cyclases than the bacterial crtY-type of lycopene cyclases.

Example 4

Carotenoid Pigments Produced by Rhodococcus Strains

*Rhodococcus erythropolis* strains ATCC 47072 and AN12 are naturally pigmented. The pink color of the two strains indicates production of carotenoid pigments in these two strains. The carotenoid pigments in ATCC 47072 and AN12 were extracted and analyzed by HPLC. For each *Rhodococcus* strain, 100 ml of cell culture in NBYE (0.8% nutrient broth+0.5% yeast extract) were grown at 26° C. overnight with shaking to the stationary phase. Cells were spun down at 4000 g for 15 min, and the cell pellets were resuspended in 10 ml acetone. Carotenoids were extracted into acetone with constant shaking at room temperature. After 1 hour, the cells were spun down at the same condition as above and the supernatant was collected. The extraction was repeated once, and the supernatants of both extractions were combined and dried under nitrogen. The dried material was re-dissolved in 0.5 ml methanol and insoluble material was removed by centrifugation at 16,000 g for 2 min in an Eppendorf microcentrifuge 5415C. 0.1 ml of the sample was used for HPLC analysis.

A Beckman System Gold® HPLC with Beckman Gold Nouveau Software (Columbia, Md.) was used for the study. 0.1 ml of the crude acetone extraction was loaded onto a 125×4 mm RP8 (5 µm particles) column with corresponding guard column (Hewlett-Packard, San Fernando, Calif.). The flow rate was 1 ml/min. Solvent program is: 0–11.5 min 40% water/60% methanol, 11.5–20 min 100% methanol, 20–30 min 40% water/60% methanol. The spectrum data were collected by the Beckman photodiode array detector (model 168).

The *Rhodococcus* strains ATCC 47072 and AN12 showed very similar profiles of the carotenoid pigments (FIG. 2) by HPLC analysis. They both had a major HPLC peak with an elution time of 14.6 min when monitored at 450 nm. The absorption maximum of the major peak is 465 nm. A minor peak was also present in both strains with an elution time of 15.6 min. The absorption maxima of the minor peak are 435 nm, 458 nm, and 486 nm. These data indicate the presence of similar or identical carotenoids in these two *Rhodococcus* strains. The molecular weight of the major and the minor carotenoids in these two strains was also determined. Carotenoids were extracted into methanol from the cell pellet and saponified with 5% KOH in methanol overnight at room temperature. After saponification, the majority of carotenoids were extracted into hexane. The extracted sample was first passed through a silica gel column to separate from neutral lipids. The column (1.5 cm×20 cm) was packed with silica gel 60 (particle size 0.040–0.063 mm, EM Science, Gibbstown, N.J.) and washed with hexane. The carotenoids sample was loaded, washed with 95% hexane+5% acetone and eluted with 80% hexane+20% acetone. The eluted carotenoids were further separated on a reverse phase C18 thin layer chromatography (TLC) plate (J. T. Baker, Phillipsburg, N.J.) with 80% acetonitrile+20% acetone as the mobile phase. The major carotenoid band (Rf 0.5) was excised and eluted with acetone. The molecular weight (MW) of the purified major carotenoid peak of ATCC 47072 was determined by MALDI-MS to be 550 Dalton. This was confirmed by LC-MS with APCI (atmospheric pressure chemical ionization) that showed the MW of the protonated compound to be 551 Dalton. LC/MS also showed the molecular weight of the minor peak carotenoid of ATCC 47072 to be 536 dalton (537 dalton for the protonated form). Mass spectrometry analysis of carotenoids from AN12 showed that the molecular weight of the major peak carotenoid (550 dalton) and the minor peak carotenoid (536 dalton) of AN12 were identical to those of ATCC 47072. Based on the HPLC result, the spectrum analysis and the molecular weight determination, it is likely that carotenoids produced by AN12 and ATCC 47072 are identical and the genes involved in the carotenoids production are homologous. The structures of the carotenoids have not yet been determined.

Example 5

Increased Carotenoids Production with Multicopy Expression of Dxs

The dxs gene encodes the 1-deoxyxylulose-5-phosphate synthase that catalyzes the first step of the synthesis of 1-deoxyxylulose-5-phosphate from glyceraldehyde-3-phosphate and pyruvate precursors in the isoprenoid pathway. An effort was made to express the putative dxs gene from AN12 on a multicopy shuttle vector and determine the effect of the dxs expression on the carotenoids production. The dxs gene with its native promoter was amplified from Rhodococcus AN12 strain by PCR. Two upstream primers, New dxs 5' primer: 5'-ATT TCG TTG AAC GGC TCG CC-3' (SEQ ID NO:24) and New2 dxs 5' primer: 5'-CGG CAA TCC GAC CTC TAC CA-3' (SEQ ID NO:25), were designed to include the native promoter region of dxs with different lengths. The downstream primer, New dxs 3' primer: 5'-TGA GAC GAG CCG <u>TCA</u> GCC TT-3 (SEQ ID NO:26)' included the underlined stop codon of the dxs gene. PCR amplification of AN12 total DNA using New dxs 5'+New dxs 3' yielded one product of 2519 bp in size, which included the full length AN12 dxs coding region and about 500 bp of immediate upstream region (nt. #500–#3019). When using New2 dxs 5'+New dxs 3' primer pair, the PCR product is 2985 bp in size, including the complete AN12 dxs gene and about 1 kb upstream region (nt. #34–#3019). Both PCR products were first cloned in the pCR2.1-TOPO cloning vector according to manufacturer's instruction (Invitrogen, Carlsbad, Calif.). Resulting clones were screened and sequenced. The confirmed plasmids were digested with EcoRI and the 2.5 kb and 3.0 kb fragments containing the dxs and the upstream region from each plasmid were treated with the Klenow enzyme and cloned into the unique Ssp I site in the *E. coli—Rhodococcus* shuttle plasmid pRhBR171 (CL1709). The resulting constructs pDCQ22 (clones #4 and #7) and pDCQ23 (clones #10 and #11) were electroporated into *Rhodococcus erythropolis* ATCC 47072 with tetracycline 10 µg/ml selection. The pigment of the *Rhodococcus* transformants appeared darker comparing to the vector control. To quantify the carotenoid production of each *Rhodococcus* strain, 1 ml of fresh cultured cells were added to 200 ml fresh LB medium with 0.05% Tween-80 and 10 µg/ml tetracycline, and grew at 30° C. for 3 days to stationary phase. Cells were pelleted by spinning at 4000 g for 15 min and the wet weight was measured for each cell pellet. Carotenoids were extracted from the cell pellets into 10 ml acetone overnight with shaking and quantitated at the absorbance maximum (465 nm) of the major carotenoid of ATCC 47072 spectrophotometrically. The absorption indicating the amount of carotenoids produced was normalized in each strain based on the cell paste weight or the cell density (OD600). Carotenoids production calculated by either method showed about 1.6-fold increase in ATCC 47072 with pDCQ22, which contains the dxs with the shorter promoter region. Carotenoid production increased even more (2.2-fold) when dxs was expressed with the longer promoter region. It is likely that the 1 kb upstream DNA contains the promoter and some elements for enhancement of the expression. HPLC analysis also verified that the same carotenoids were produced in the dxs expression strain as those of the wild type strain.

TABLE 2

Carotenoids production by Rhodococcus strains.

| Strain | OD600 | weight (g) | OD465 | %[a] | % (Wt)[b] | % (OD600)[c] | % (avg)[d] |
|---|---|---|---|---|---|---|---|
| ATCC 47072 (pRhBR171) | 1.992 | 2.82 | 0.41 | 100 | 100 | 100 | 100 |
| ATCC (pDCQ22)#4 | 1.93 | 2.9 | 0.642 | 157 | 161 | 152 | 156 |
| ATCC (pDCQ22)#7 | 1.922 | 2.76 | 0.664 | 162 | 159 | 156 | 157 |
| ATCC (pDCQ23)#10 | 1.99 | 2.58 | 0.958 | 234 | 214 | 233 | 224 |
| ATCC (pDCQ23)#11 | 1.994 | 2.56 | 0.979 | 239 | 217 | 239 | 228 |

[a]% of carotenoid production based on OD465 nm.
[b]% of carotenoid production (OD465 nm) normalized with wet cell paste weight.
[c]% of carotenoid production (OD465 nm) normalized with cell density (OD600 nm).
[d]% of carotenoid production (OD465 nm) averaged from the normalizations with wet cell paste weight and cell density.

Example 6

Loss of Carotenoid Pigment in the Rhodococcus CrtE or CrtI Mutant

Figure 3:
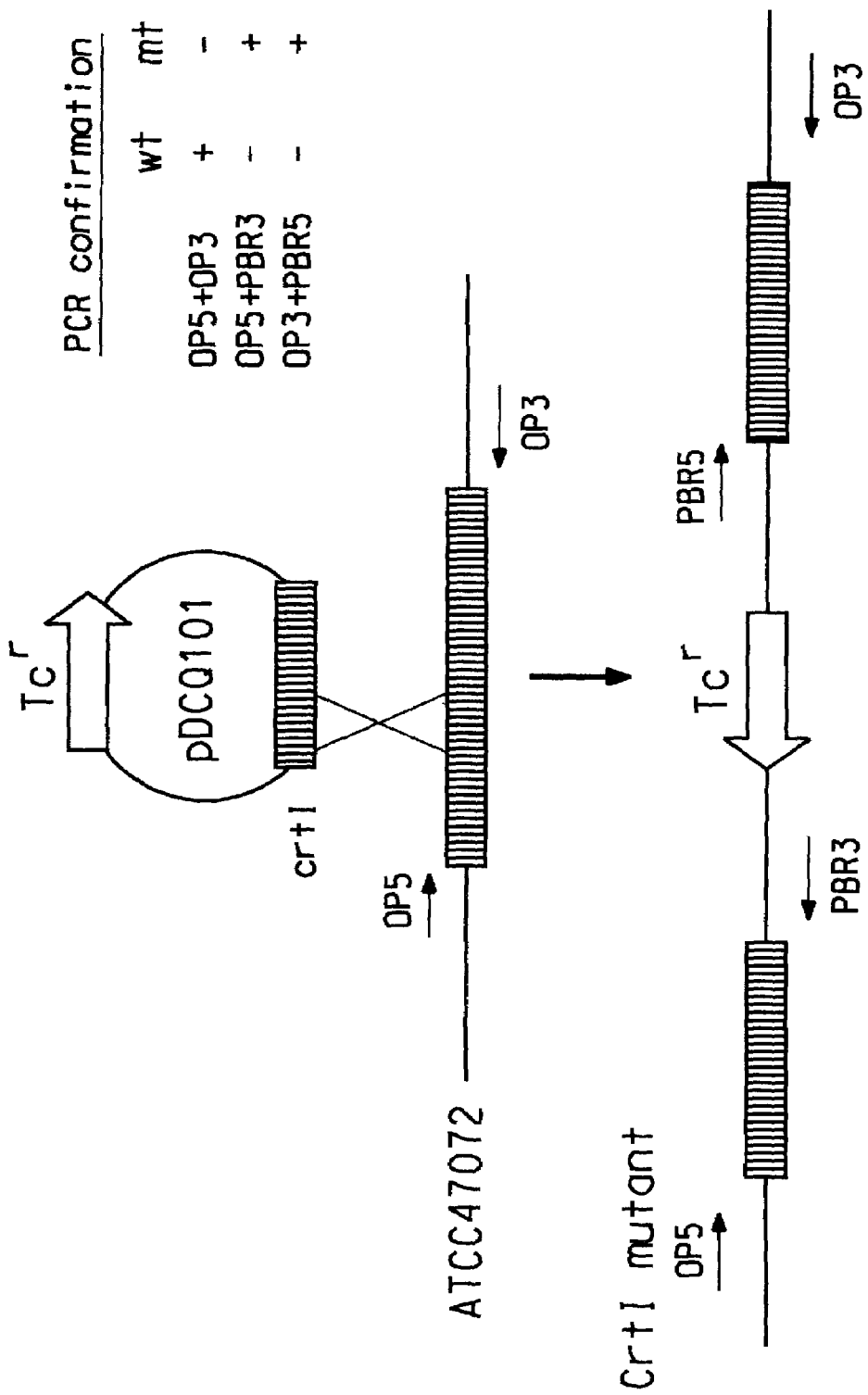
FIG. 3 shows the targeted gene disruption by homologous recombination using the crtI gene as an example.

To confirm the functions of some of the genes listed in Table 1 for carotenoid biosynthesis, gene disruption mutants of crtE and crtI were constructed by homologous recombination. The targeted gene disruption scheme is shown in FIG. 3 using crtI as an example. PCR primers designed based on the crtE and crtI sequences of AN12 were used to amplify internal fragments of crtE and crtI from ATCC 47072. The primers AN12_E_F (5'-CATGCCATGGCCTC-GAAGCCTTCGTCCTG-3') (SEQ ID NO:27) and AN12_E_R (5'-CATGCCATGGCGCAGAGTGTCGACT-TCGTT-3') (SEQ ID NO:28) amplified 801 bp crtE with 179 bp truncation at N terminal and 160 bp truncation at C terminal. The primers AN12_I_F (5'-TTCATGCCATG-GACTCGTCGAAGACGCTCTTG-3') (SEQ ID NO:29) and AN12_I_R (5'-TTCATGCCATGGTGACGAGCAGT-GACGGAT-3') (SEQ ID NO:30) amplified 910 bp crtI with 221 bp truncation at N terminal and 462 bp truncation at C terminal. The crtE and crtI fragments amplified from ATCC 47072 were confirmed by sequencing and showed about 95% identity on the DNA level to the crtE and crtI of AN12. The crtE fragment and the crtI fragment were first cloned into pCR2.1 TOPO vector (Invitrogen, Carlsbad, Calif.). The TOPO clones were then digested with NcoI (restriction sites underlined in the primer sequences) and the crtE or crtI fragments were subsequently cloned into the NcoI site of pBR328. The resulting constructs were confirmed by sequencing and designated as pDCQ100 for the crtE clone and pDCQ101 for the crtI clone. Approximately 1 μg DNA of pDCQ100 and pDCQ101 were introduced into *Rhodococcus* ATCC 47072 by electroporation and plated on NBYE plates with 10 μg/ml tetracycline. The pBR328 vector does not replicate in *Rhodococcus*. The tetracycline resistant transformants obtained after 3–4 days of incubation at 30° C. were generated by chromosomal integration. Integration into the targeted crtE or crtI gene on chromosome of ATCC 47072 was confirmed by PCR. The vector specific primers PBR3 (5'-AGCGGCATCAGCACCTTG-3') (SEQ ID NO:31) and PBR5 (5'-GCCAATATGGA-CAACTTCTTC-3') (SEQ ID NO:32), paired with the gene specific primers (outside of the insert on pDCQ100 or pDCQ101) E_OP5 (5'-ATCCGACCTCACTCGAACTGC-CAG-3') (SEQ ID NO:33) and E_OP3 (5'-GGTCGGC-GAGCTGACGGTTCGAGT-3') (SEQ ID NO:34) or I_OP5 (5'-CGGCCACGAAGCGAAGCTACTGAC-3') (SEQ ID NO:35) and I_OP3 (5'-ATCGTGGATGAATGGTCGGT-TACG-3') (SEQ ID NO:36), were used for PCR using chromosomal DNA prepared from the tetracycline resistant transformants as the templates. PCR fragments of the expected sizes were amplified from the tetracycline resistant transformants, but no PCR product was obtained from the wild type ATCC 47072. When the two gene specific primers were used, no PCR fragment was obtained with the tetracycline resistant transformant due to the insertion of the large vector DNA. The PCR fragments obtained with the vector specific primers and the gene specific primers were sequenced. Sequence analysis of the junction of the vector and the cftE or cftI gene confirmed that the single crossover recombination occurred at the expected sites and disrupted the target genes crtE or crtI.

Next the phenotypes of the CrtE and CrtI disruption mutants of ATCC 47072 were analyzed. Colonies of CrtE or CrtI disruption mutants were pale white. It appeared that the pigments present in the wild type strain were lost in both mutants. HPLC analysis of the carotenoids of the mutants confirmed the visual inspection result. HPLC analysis was performed as described in Example 4. The CrtI disruption mutant did not have the two HPLC peaks present in the wild type strains when monitored at 450 nm. It showed a HPLC peak at elution time of 15.8 min when monitored at 286 nm. The absorption maxima of this peak are 276 nm, 286 nm, 297 nm, which is identical to that of phytoene. This peak was not present in the wild type strain. These results confirmed the role of CrtI in carotenoids biosynthesis. Knockout of the CrtI resulted in no carotenoid pigment as represented by the two HPLC peaks at 450 nm. Phytoene (colorless) accumulation in the CrtI mutant confirms the function of CrtI as the phytoene dehydogenase as suggested by the BLAST search. The CrtE mutant had neither the two HPLC peaks present in the wild type nor the phytoene peak in the CrtI mutant. These results also confirmed the role of CrtE in carotenoids biosynthesis. No phytoene accumulation in CrtE was consistent with the function of CrtE as geranylgeranyl pyrophosphate synthase, which acts prior to the phytoene synthesis step in the pathway.

TABLE 3

Summary of the phenotypes of the Crt knockout mutants of ATCC 47072

| Strain | Colony color | Carotenoids analysis by HPLC (450 nm) | Phytoene intermediate |
|---|---|---|---|
| Wild type | Pink | Major (465 nm) at 14.6 min<br>Minor (435 nm, 458 nm, 486 nm) at 15.6 min | No |
| CrtI | White | No peaks | Yes |
| CrtE | White | No peaks | No |

Example 7

Inhibition of the CrtL-type of Lycopene Cyclase in Rhodococcus

Since the lycopene cyclase identified in *Rhodococcus erythropolis* strain AN12 showed high sequence similarity to the CrtL-type of lycopene cyclases in plants and cyanobacterium (Example 3), it was decided to determine if the lycopene cyclase in *Rhodococcus* was also functionally related to the CrtL-type of lycopene cyclases. The tri-alkyl amine compounds, 2-(4-methylphenoxy)-triethylamine hydrochloride (MPTA) and 2-(4-chlorophenylthio)-triethylamine hydrochloride (CPTA), have been shown to specifically inhibit the CrtL-type of lycopene cyclases and not the nonphotosynthetic bacterial CrtY-type of lycopene cyclases (Cunningham, Jr., et al, Molecular structure and enzymatic function of lycopene cyclase from the Cyanobacterium Synechococcus sp. strain PCC7942, The *Plant Cell*, 1994, Vol. 6:1107). An examination was made of the effect of MPTA or CPTA on carotenoid production in *Rhodococcus erythropolis*. One ml of overnight cultured ATCC 47072 cells were added to 200 ml LB medium with 0.05% Tween-80 without or with 40 μM CPTA or MPTA inhibitor, and cultured at 30° C. with shaking for 24 hr. Cells were spun down at 4000 g for 15 min, and the cell pellet was resuspended in 10 ml acetone. Carotenoids were extracted into acetone with constant shaking at room temperature for 1 hr followed by spinning down the cell debris at 4000 g for 15 min. The extraction was repeated once, and the supernatants of both extractions were combined and dried under nitrogen. The dried material was re-dissolved in 1 ml methanol and insoluble material was removed by spinning at 16,000 g for 2 min in a microcentrifuge. 0.1 ml of the sample was used for HPLC analysis as described in Example 4. Results are summarized in Table 4.

In the absence of any inhibitor, *Rhodococcus* ATCC 47072 produced the same carotenoids as described in Example 4. In the presence of 40 μM CPTA or MPTA, the major peak appeared at 15.3 min with the absorption spectra as 443, 469, 500 nm. The authentic lycopene standard from Sigma (St. Louis, Mo.) showed similar properties under the same conditions (eluted at 15.3 min with the peak spectra as 443, 469, 500 nm). These confirmed that lycopene is the substrate of the cyclase in *Rhodococcus* and the *Rhodococcus* lycopene cyclase could be inhibited by the inhibitors specific for the CrtL-type of cyclases in photosynthetic bacteria and plants. In the presence of 40 μM CPTA, the inhibition was estimated to be 95%, and small amount (5% of total carotenoids) of the wild type major carotenoid was still observed. In the presence of 40 μM MPTA, the inhibition was estimated to be 82%, and 18% of the total carotenoids was the wild type major carotenoid.

TABLE 4

Inhibition of lycopene cyclase in Rhodococcus ATCC 47072.

| ATCC 47072 | Major peak | Minor peak |
|---|---|---|
| No inhibitor | 14.6 min (465 nm)<br>87% | 15.6 min (437, 459, 486 nm)<br>13% |
| 40 μM CPTA | 15.3 min (443, 469, 500 nm)<br>95% | 14.5 min (465 nm)<br>5% |
| 40 μM MPTA | 15.3 min (443, 469, 500 nm)<br>82% | 14.5 min (465 nm)<br>18% |

What is claimed is:

1. An isolated nucleic acid molecule selected from the group consisting of:
   (a) an isolated nucleic acid molecule encoding an isoprenoid biosynthetic enzyme, having the amino acid sequence of SEQ ID NO:2; and
   (b) the isolated nucleic acid molecule that is complementary to (a).

2. The isolated nucleic acid molecule of claim 1 of SEQ ID NO:1.

3. A chimeric gene comprising the isolated nucleic acid molecule of claim 1 operably linked to suitable regulatory sequences.

4. A transformed host cell comprising the chimeric gene of claim 3.

5. The transformed host cell of claim 4 wherein the host cell is selected from the group consisting of bacteria, yeast, filamentous fungi, algae, and green plants.

6. The transformed host cell of claim 5 wherein the host cell is selected from the group consisting of *Aspergillus, Trichoderma, Saccharomyces, Pichia, Candida, Hansenula,* or bacterial species such as *Salmonella, Bacillus, Acinetobacter, Zymomonas, Agrobactereium, Erythrobacter, Chiorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobtuin, Methylocysis, Alcaligenes, Synechocystis, Synechococcus, Anabaena, Myxococcus, Thiobacillus, Methanobacterium and Klebsiella.*

7. The transformed host cell of claim 5 wherein the host cell is selected from the group consisting of *Spirulina, Haemotacoccus,* and *Dunalliela.*

8. The transformed host cell of claim 5 wherein the host cell is selected from the group consisting of soybean, rapeseed, sunflower, cotton, corn, tobacco, alfalfa, wheat barley, oats, sorghum, rice, *Arabidopsis*, cruciferous vegetables, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

* * * * *

SEQUENCE LISTING

<160> NUMBER OF SEQ ID NOS: 36

<210> SEQ ID NO 1
<211> LENGTH: 1947
<212> TYPE: DNA
<213> ORGANISM: Rhodococcus erythropolis

<400> SEQUENCE: 1

```
ttgggtgttc ttgcccgcat tcagggtcct gacgatctac gtcagttgag ccacgccgag      60
atgacggagt tggccgacga gattcgtgag ttcctcgtgc tgaaggtcgc tgcgaccggt     120
ggtcacctcg ggcccaactt gggcgtcgtg gagttgaccc tcgcactgca ccgaattttc     180
gactcgccgc aggacgcgat catcttcgac acgggccatc aggcctacgt gcacaagatc     240
ctcaccggtc gtcaggatca gttcgacact ctgcgtaagc agggcggact gtccgggtat     300
ccgtgccgcg ccgagagcga acacgactgg gtcgagtcct ctcacgcttc cgccgcgttg     360
```

```
tcctatgccg acggcctcgc gaaggccttc gcgctcacgg ccagaatcg ccacgttgtc      420 gccgtcgtcg gtgacggcgc cctgaccggc ggaatgtgtt gggaagccct caacaacatc      480
gcagccggaa agaccgttc ggtggtgatc gtcgtcaacg acaacggccg ctcgtacgcg       540
ccgaccatcg gcggcctcgc cgaccatctt tcggcactgc gcaccgcgcc gagttacgag      600
cgcgccctcg acagtggccg acgcatggtc aagagactgc cctgggtggg gcgcaccgcg      660
tactccgtcc tgcacggaat gaaggcgggt ctcaaggacg ctgtcagccc tcaggtcatg      720
ttcaccgatc tgggtatcaa gtacctcgga ccggtcgacg gtcacgacga agccgccatg      780
gaatcggcgt tgcgccgggc gaaggcctac ggcggaccgg tcatcgttca tgccgtcact      840
cgtaagggca acggttacgc acacgccgag aacgacgtgg ccgaccagat gcatgccacc      900
ggcgtcatcg atcccgtcac cggtcgcggc accaagtcgt ccgcgccgga ctggacgtcg      960
gtcttctcgg ccgcattgat cgagcaggct tcgcgtcgtg aggacattgt cgccatcacc     1020
gcggcgatgg ccgggcccac cggcctcgcg gccttcgggg agaagttccc cgatcggatt     1080
ttcgacgtcg gtatcgccga gcagcatgcg atgacctcgg ccgccggtct tgcacttggc     1140
ggacttcacc ccgtcgttgc tatctactcg accttcctca atcgggcttt cgaccagttg     1200
ttgatggacg tcgcactgct caaacaaccg gtgacagtcg tgctcgaccg cgccggggtc     1260
accggagtcg acggcgccag ccacaacggc gtctgggatc tttcgctgct cggaatcatc     1320
ccggggattc gcgtcgcggc accgcgtgat gcagacacac tgcgggaaga gttggacgag     1380
gcgcttctcg tcgacgacgg cccaacggtc gtacggttcc cgaagggtgc tgtacccgaa     1440
gcgattccgg cagtgaagcg actcgacgga atggtcgacg tcctcaaggc agcgagggt     1500 gagcgcggcg acgtgctcct cgtcgcggtg ggcccatttg catccttggc gctcgagatt     1560
gccgagcggc tcgacaagca gggcatctcg gttgccgtcg ttgatccgcg atgggttctg     1620 ccggtcgcg attcgctggt gaagatggcg gacaagtacg ccctcgtggt caccatcgaa     1680
gacggcggtt tgcacggcgg catcggttcg acggtctcgg ccgcgatgcg tgccgccgga     1740
gtgcacacgt cgtgccgcga catgggcgtt ccccagcagt tcctcgatca cgccagccgc     1800
gaagccatcc acaaggaact cggactcacg gctcaggacc tctcccgcaa gatcaccggc     1860
tgggtggcgg ggatgggcag cgtcggcgtc cacgtccagg aagacgcgtc ctcggcttcg     1920
gctcagggcg aagtcgcgca aggctga                                         1947
```

<210> SEQ ID NO 2
<211> LENGTH: 648
<212> TYPE: PRT
<213> ORGANISM: Rhodococcus erythropolis

<400> SEQUENCE: 2

Met Gly Val Leu Ala Arg Ile Gln Gly Pro Asp Asp Leu Arg Gln Leu
1               5                   10                  15

Ser His Ala Glu Met Thr Glu Leu Ala Asp Glu Ile Arg Glu Phe Leu
                20                  25                  30

Val Leu Lys Val Ala Ala Thr Gly Gly His Leu Gly Pro Asn Leu Gly
            35                  40                  45

Val Val Glu Leu Thr Leu Ala Leu His Arg Ile Phe Asp Ser Pro Gln
        50                  55                  60

Asp Ala Ile Ile Phe Asp Thr Gly His Gln Ala Tyr Val His Lys Ile
65                  70                  75                  80

Leu Thr Gly Arg Gln Asp Gln Phe Asp Thr Leu Arg Lys Gln Gly Gly

-continued

```
                85                  90                  95
Leu Ser Gly Tyr Pro Cys Arg Ala Glu Ser Glu His Asp Trp Val Glu
            100                 105                 110

Ser Ser His Ala Ser Ala Ala Leu Ser Tyr Ala Asp Gly Leu Ala Lys
            115                 120                 125

Ala Phe Ala Leu Thr Gly Gln Asn Arg His Val Val Ala Val Val Gly
            130                 135                 140

Asp Gly Ala Leu Thr Gly Gly Met Cys Trp Glu Ala Leu Asn Asn Ile
145                 150                 155                 160

Ala Ala Gly Lys Asp Arg Ser Val Val Ile Val Val Asn Asp Asn Gly
                165                 170                 175

Arg Ser Tyr Ala Pro Thr Ile Gly Gly Leu Ala Asp His Leu Ser Ala
            180                 185                 190

Leu Arg Thr Ala Pro Ser Tyr Glu Arg Ala Leu Asp Ser Gly Arg Arg
            195                 200                 205

Met Val Lys Arg Leu Pro Trp Val Gly Arg Thr Ala Tyr Ser Val Leu
            210                 215                 220

His Gly Met Lys Ala Gly Leu Lys Asp Ala Val Ser Pro Gln Val Met
225                 230                 235                 240

Phe Thr Asp Leu Gly Ile Lys Tyr Leu Gly Pro Val Asp Gly His Asp
            245                 250                 255

Glu Ala Ala Met Glu Ser Ala Leu Arg Arg Ala Lys Ala Tyr Gly Gly
            260                 265                 270

Pro Val Ile Val His Ala Val Thr Arg Lys Gly Asn Gly Tyr Ala His
            275                 280                 285

Ala Glu Asn Asp Val Ala Asp Gln Met His Ala Thr Gly Val Ile Asp
            290                 295                 300

Pro Val Thr Gly Arg Gly Thr Lys Ser Ser Ala Pro Asp Trp Thr Ser
305                 310                 315                 320

Val Phe Ser Ala Ala Leu Ile Glu Gln Ala Ser Arg Arg Glu Asp Ile
            325                 330                 335

Val Ala Ile Thr Ala Ala Met Ala Gly Pro Thr Gly Leu Ala Ala Phe
            340                 345                 350

Gly Glu Lys Phe Pro Asp Arg Ile Phe Asp Val Gly Ile Ala Glu Gln
            355                 360                 365

His Ala Met Thr Ser Ala Ala Gly Leu Ala Leu Gly Gly Leu His Pro
            370                 375                 380

Val Val Ala Ile Tyr Ser Thr Phe Leu Asn Arg Ala Phe Asp Gln Leu
385                 390                 395                 400

Leu Met Asp Val Ala Leu Leu Lys Gln Pro Val Thr Val Val Leu Asp
                405                 410                 415

Arg Ala Gly Val Thr Gly Val Asp Gly Ala Ser His Asn Gly Val Trp
            420                 425                 430

Asp Leu Ser Leu Leu Gly Ile Ile Pro Gly Ile Arg Val Ala Ala Pro
            435                 440                 445

Arg Asp Ala Asp Thr Leu Arg Glu Glu Leu Asp Glu Ala Leu Leu Val
            450                 455                 460

Asp Asp Gly Pro Thr Val Val Arg Phe Pro Lys Gly Ala Val Pro Glu
465                 470                 475                 480

Ala Ile Pro Ala Val Lys Arg Leu Asp Gly Met Val Asp Val Leu Lys
                485                 490                 495

Ala Ser Glu Gly Glu Arg Gly Asp Val Leu Leu Val Ala Val Gly Pro
            500                 505                 510
```

```
Phe Ala Ser Leu Ala Leu Glu Ile Ala Glu Arg Leu Asp Lys Gln Gly
        515                 520                 525

Ile Ser Val Ala Val Asp Pro Arg Trp Val Leu Pro Val Ala Asp
    530                 535                 540

Ser Leu Val Lys Met Ala Asp Lys Tyr Ala Leu Val Val Thr Ile Glu
545                 550                 555                 560

Asp Gly Gly Leu His Gly Gly Ile Gly Ser Thr Val Ser Ala Ala Met
                565                 570                 575

Arg Ala Ala Gly Val His Thr Ser Cys Arg Asp Met Gly Val Pro Gln
                580                 585                 590

Gln Phe Leu Asp His Ala Ser Arg Glu Ala Ile His Lys Glu Leu Gly
        595                 600                 605

Leu Thr Ala Gln Asp Leu Ser Arg Lys Ile Thr Gly Trp Val Ala Gly
        610                 615                 620

Met Gly Ser Val Gly Val His Val Gln Glu Asp Ala Ser Ser Ala Ser
625                 630                 635                 640

Ala Gln Gly Glu Val Ala Gln Gly
                645
```

```
<210> SEQ ID NO 3
<211> LENGTH: 1158
<212> TYPE: DNA
<213> ORGANISM: Rhodococcus erythropolis

<400> SEQUENCE: 3
gtgcaggaaa ccacacgtac ccgcgtcctc ctcctcggca gtaccggttc gatcggtacc    60
caagcgctgg aggtcatcgc agccaacccc gatcgtttcg aagtagtcgg tctcgcagcg   120
ggcggcaaca acgtcgagtt gttgggcgaa cagattcgtg caaccggcgt cacggacgtc   180
gccgtcgccg atcctgcagc ggcatcggcg ctggaatcgg taaccgcccg ttcgggaccg   240
agcgccgtga cggaactggt tcgggacagc ggtgccgatg ttgtcctcaa tgcactcgtc   300
ggttcgttgg gactcgaacc gactctggcg gcgctgaact cgggagcgcg cctggcgctg   360
gcgaacaagg aatcgcttgt cgccggcgga gcgctggtga ccaaagccgc cgcacccggt   420
cagatcgtgc cggtcgactc ggagcattcg gcgcttgccc agtgtctacg tggtggaaca   480
ggcgacgaag tggctcggtt ggttctcacc gcttcgggtg accgttccg tggctggagc    540
gccgaggatc tcgaaagtgt gaatccagct caggcaaaag cgcacccac ctggtcgatg    600
gggcccatga acaccctcaa ttcggcaact ctggtcaaca agggcctcga gctgatcgag   660
acgaacctgc tgttcgggat cgactacgac cgcatcgacg tcaccgtgca cccgcagtcg   720
atcgtgcatt ccatggtgac cttcttcgac gggtcgacgc tggcacaggc aagcccgccg   780
gacatgaagc tcccgatcgc tctcgctctc ggctggccgg accgcatcga aggtgctgcg   840
tcggcatgcg acttcaccac cgcctccacc tgggaattcg agccgctcga ttcgtcggtg   900
ttccccgccg tcgatctggc gcgaagcgcg ggcaaatccg gcggttgctt caccgcgatc   960
tacaacgcgc ccaacgaagt ggcggctcag gcattcctcg acggtgtcat ttccttcccg  1020
gcgatcgtcc gcacggtggc cgctgttctc gacgatgcag gtcaatggtc cgcggaaccg  1080
gttaccgtgg acgacgttct ggccgcagac ggctgggcac gcacacgagc gcgtcagctc  1140
gtgaagcagg agggctag                                                 1158

<210> SEQ ID NO 4
<211> LENGTH: 385
```

```
<212> TYPE: PRT
<213> ORGANISM: Rhodococcus erythropolis

<400> SEQUENCE: 4

Met Gln Glu Thr Thr Arg Thr Arg Val Leu Leu Gly Ser Thr Gly
1               5                   10                  15

Ser Ile Gly Thr Gln Ala Leu Glu Val Ile Ala Ala Asn Pro Asp Arg
            20                  25                  30

Phe Glu Val Val Gly Leu Ala Ala Gly Gly Asn Asn Val Glu Leu Leu
                35                  40                  45

Gly Glu Gln Ile Arg Ala Thr Gly Val Thr Asp Val Ala Val Ala Asp
50                  55                  60

Pro Ala Ala Ala Ser Ala Leu Glu Ser Val Thr Ala Arg Ser Gly Pro
65                  70                  75                  80

Ser Ala Val Thr Glu Leu Val Arg Asp Ser Gly Ala Asp Val Val Leu
                85                  90                  95

Asn Ala Leu Val Gly Ser Leu Gly Leu Glu Pro Thr Leu Ala Ala Leu
            100                 105                 110

Asn Ser Gly Ala Arg Leu Ala Leu Ala Asn Lys Glu Ser Leu Val Ala
            115                 120                 125

Gly Gly Ala Leu Val Thr Lys Ala Ala Pro Gly Gln Ile Val Pro
130                 135                 140

Val Asp Ser Glu His Ser Ala Leu Ala Gln Cys Leu Arg Gly Gly Thr
145                 150                 155                 160

Gly Asp Glu Val Ala Arg Leu Val Leu Thr Ala Ser Gly Gly Pro Phe
                165                 170                 175

Arg Gly Trp Ser Ala Glu Asp Leu Glu Ser Val Asn Pro Ala Gln Ala
            180                 185                 190

Lys Ala His Pro Thr Trp Ser Met Gly Pro Met Asn Thr Leu Asn Ser
            195                 200                 205

Ala Thr Leu Val Asn Lys Gly Leu Glu Leu Ile Glu Thr Asn Leu Leu
            210                 215                 220

Phe Gly Ile Asp Tyr Asp Arg Ile Asp Val Thr Val His Pro Gln Ser
225                 230                 235                 240

Ile Val His Ser Met Val Thr Phe Phe Asp Gly Ser Thr Leu Ala Gln
                245                 250                 255

Ala Ser Pro Pro Asp Met Lys Leu Pro Ile Ala Leu Ala Leu Gly Trp
            260                 265                 270

Pro Asp Arg Ile Glu Gly Ala Ala Ser Ala Cys Asp Phe Thr Thr Ala
            275                 280                 285

Ser Thr Trp Glu Phe Glu Pro Leu Asp Ser Ser Val Phe Pro Ala Val
290                 295                 300

Asp Leu Ala Arg Ser Ala Gly Lys Ser Gly Gly Cys Phe Thr Ala Ile
305                 310                 315                 320

Tyr Asn Ala Ala Asn Glu Val Ala Ala Gln Ala Phe Leu Asp Gly Val
                325                 330                 335

Ile Ser Phe Pro Ala Ile Val Arg Thr Val Ala Val Leu Asp Asp
            340                 345                 350

Ala Gly Gln Trp Ser Ala Glu Pro Val Thr Val Asp Val Leu Ala
            355                 360                 365

Ala Asp Gly Trp Ala Arg Thr Arg Ala Arg Gln Leu Val Lys Gln Glu
370                 375                 380

Gly
385
```

<210> SEQ ID NO 5
<211> LENGTH: 699
<212> TYPE: DNA
<213> ORGANISM: Rhodococcus erythropolis

<400> SEQUENCE: 5

| | | | | | |
|---|---|---|---|---|---|
| gtggcagtag | tagccctggt | acctgccgca | ggtcggggag | tgcgattggg | cgagaaattg | 60 |
| cccaaggcat | ttgtcgaact | cggtgggtgc | accatgcttg | cacgcgcggt | cgatggactc | 120 |
| cggaaatccg | gagcgatcga | ccgcgttgtt | gtcattgtgc | cgcctgaact | ggtcgaatcc | 180 |
| gtcgtggccg | acctcggtcg | tgcatcggac | gtcgacgtcg | tcggtggtgg | tgccgaaaga | 240 |
| accgattcgg | ttcgagccgg | tctcagtgct | gccggcgacg | cagattttgt | actcgtgcac | 300 |
| gacgccgcgc | gggcattgac | gccgccggcg | ttgatcgcgc | gcgtcgtcga | cgctctccga | 360 |
| gccggcagca | cgctgtcat | cccggtactc | ccggttaccg | acacgatcaa | gtcggtcgac | 420 |
| gtactcggcg | cagtcaccgg | aacgcctctg | cgttcggagt | tgcgtgcggt | tcaaactcct | 480 |
| caaggcttct | ccaccgacgt | cctgcgcagt | gcgtacgacg | ccggtgatgt | cgccgcgacc | 540 |
| gacgacgccg | ctctggtgga | gcgtctcggt | gtttcggtgc | agacgattcc | cggcgacgct | 600 |
| ctcgccttca | agatcaccac | tccgctcgac | ctcgtccttg | cacgggcgct | cctgatctcg | 660 |
| gagacagagt | tgagcgcgga | ctcacaggac | ggaaaatag | | | 699 |

<210> SEQ ID NO 6
<211> LENGTH: 232
<212> TYPE: PRT
<213> ORGANISM: Rhodococcus erythropolis

<400> SEQUENCE: 6

Met Ala Val Val Ala Leu Val Pro Ala Ala Gly Arg Gly Val Arg Leu
1               5                   10                  15

Gly Glu Lys Leu Pro Lys Ala Phe Val Glu Leu Gly Gly Cys Thr Met
                20                  25                  30

Leu Ala Arg Ala Val Asp Gly Leu Arg Lys Ser Gly Ala Ile Asp Arg
        35                  40                  45

Val Val Ile Val Pro Pro Glu Leu Val Glu Ser Val Val Ala Asp
    50                  55                  60

Leu Gly Arg Ala Ser Asp Val Asp Val Val Gly Gly Ala Glu Arg
65                  70                  75                  80

Thr Asp Ser Val Arg Ala Gly Leu Ser Ala Ala Gly Asp Ala Asp Phe
                85                  90                  95

Val Leu Val His Asp Ala Ala Arg Ala Leu Thr Pro Pro Ala Leu Ile
                100                 105                 110

Ala Arg Val Asp Ala Leu Arg Ala Gly Ser Ser Ala Val Ile Pro
        115                 120                 125

Val Leu Pro Val Thr Asp Thr Ile Lys Ser Val Asp Val Leu Gly Ala
    130                 135                 140

Val Thr Gly Thr Pro Leu Arg Ser Glu Leu Arg Ala Val Gln Thr Pro
145                 150                 155                 160

Gln Gly Phe Ser Thr Asp Val Leu Arg Ser Ala Tyr Asp Ala Gly Asp
                165                 170                 175

Val Ala Ala Thr Asp Asp Ala Ala Leu Val Glu Arg Leu Gly Val Ser
                180                 185                 190

Val Gln Thr Ile Pro Gly Asp Ala Leu Ala Phe Lys Ile Thr Thr Pro
        195                 200                 205

```
Leu Asp Leu Val Leu Ala Arg Ala Leu Leu Ile Ser Glu Thr Glu Leu
        210                 215                 220

Ser Ala Asp Ser Gln Asp Gly Lys
225                 230

<210> SEQ ID NO 7
<211> LENGTH: 936
<212> TYPE: DNA
<213> ORGANISM: Rhodococcus erythropolis

<400> SEQUENCE: 7
gtgctctccg tcgttcctcg ccccgtagtt gtccgggccc cgtccaaggt gaatctccac      60
cttgccgtcg gggacctgcg agacgacggc tatcacgaac tgacgaccgt ttttcaggca     120
ttgtcgctgg cagacactgt cacggtggcg cctgcggaca ccttgaccgt gcgggtgatc     180
ggcgacgacg ccgcgccgt accgaccgat cgcaccaatc tcgtgtggcg tgccgccgag     240
atgcttgcgg ccgagggtgg cgtggccccg aatgtcgaga tcgtcatcga agggcatt      300
cccgtcgcag gcggtatggc cggcgggagc gccgacgcgg cagccgcgtt ggttgcgctc     360
aattcgttgt ggaaactcga cttctcgcgg cctgatctcg acgccttcgc ggcacgtctc     420
gggagtgacg ttccgttctc gctgcacggt ggcactgccc tcgggaccgg tcgcggtgaa     480
caacttgtcc ccgtcttgac gcgccgcacc tttcactggg tgttggcgct ggccaaggga     540
ggcttgagca cgccggttgt cttccgggaa ctcgacaagc ttcgcgccga aggcacaccg     600
aatcgattgg gtaccgctga cgagttgatt cacgcgctca ccaccggtga ccctcatgtg     660
ctcgccccgc tgctcggaaa cgatctgcag gcggcagcac tctcactcaa cccggatcta     720
cgacggacgc tgcgagcggg tgtcgaagcc ggagctttgg ccggcatcgt ctccggctcc     780
ggaccgacgt gcgcctttct ctgcgccgac gcacagtccg cggtggaagt gagcgcagaa     840
cttgcgggag cggggggtgtg ccgcaccgtt cgcgtggcga gcggacccgt tcccggagca     900
cgaatactcg acaatgcggc aaagggacag cactga                              936

<210> SEQ ID NO 8
<211> LENGTH: 311
<212> TYPE: PRT
<213> ORGANISM: Rhodococcus erythropolis

<400> SEQUENCE: 8

Met Leu Ser Val Val Pro Arg Pro Val Val Arg Ala Pro Ser Lys
1               5                   10                  15

Val Asn Leu His Leu Ala Val Gly Asp Leu Arg Asp Asp Gly Tyr His
            20                  25                  30

Glu Leu Thr Thr Val Phe Gln Ala Leu Ser Leu Ala Asp Thr Val Thr
        35                  40                  45

Val Ala Pro Ala Asp Thr Leu Thr Val Arg Val Ile Gly Asp Asp Ala
    50                  55                  60

Ala Ala Val Pro Thr Asp Arg Thr Asn Leu Val Trp Arg Ala Ala Glu
65                  70                  75                  80

Met Leu Ala Ala Glu Gly Gly Val Ala Pro Asn Val Glu Ile Val Ile
                85                  90                  95

Glu Lys Gly Ile Pro Val Ala Gly Gly Met Ala Gly Gly Ser Ala Asp
            100                 105                 110

Ala Ala Ala Ala Leu Val Ala Leu Asn Ser Leu Trp Lys Leu Asp Phe
        115                 120                 125
```

```
Ser Arg Pro Asp Leu Asp Ala Phe Ala Ala Arg Leu Gly Ser Asp Val
130                 135                 140

Pro Phe Ser Leu His Gly Gly Thr Ala Leu Gly Thr Gly Arg Gly Glu
145                 150                 155                 160

Gln Leu Val Pro Val Leu Thr Arg Arg Thr Phe His Trp Val Leu Ala
            165                 170                 175

Leu Ala Lys Gly Gly Leu Ser Thr Pro Val Val Phe Arg Glu Leu Asp
            180                 185                 190

Lys Leu Arg Ala Glu Gly Thr Pro Asn Arg Leu Gly Thr Ala Asp Glu
            195                 200                 205

Leu Ile His Ala Leu Thr Thr Gly Asp Pro His Val Leu Ala Pro Leu
210                 215                 220

Leu Gly Asn Asp Leu Gln Ala Ala Leu Ser Leu Asn Pro Asp Leu
225                 230                 235                 240

Arg Arg Thr Leu Arg Ala Gly Val Glu Ala Gly Ala Leu Ala Gly Ile
            245                 250                 255

Val Ser Gly Ser Gly Pro Thr Cys Ala Phe Leu Cys Ala Asp Ala Gln
            260                 265                 270

Ser Ala Val Glu Val Ser Ala Glu Leu Ala Gly Ala Gly Val Cys Arg
            275                 280                 285

Thr Val Arg Val Ala Ser Gly Pro Val Pro Gly Ala Arg Ile Leu Asp
290                 295                 300

Asn Ala Ala Lys Gly Gln His
305                 310

<210> SEQ ID NO 9
<211> LENGTH: 477
<212> TYPE: DNA
<213> ORGANISM: Rhodococcus erythropolis

<400> SEQUENCE: 9
atgcgcgtcg gtctcggcac ggatgttcat cccatcgagg tcggccgacc ttgctggatg    60
gccgggttgc tgttcgagga agcagacggg tgctcggggc attcggacgg cgacgtcgcc   120
gtccacgcgc tctgtgacgc gttgctctcc gccgcaggtc ttggcgacct cggttcggtt   180
ttcggcaccg gcaggcccga atgggacggg gtgagcggcg ctcgaatgct tgccgaggtt   240
cgtcgactgc tcgaagagaa ccagttcacc gtcggcaacg ccgcggtgca ggtcatcggc   300
aaccgaccga gatcgggcc gcgacgcgac gaggcgcaga aggtgctctc ggacattctc   360
ggcgcgcctg tttcggtgtc cgcgaccacc acggacgggc tcggcttgac cggtcgcggc   420
gaggggatcg ccgccatggc caccgcgttg gtcatgacaa ccgaacacga caggtaa      477

<210> SEQ ID NO 10
<211> LENGTH: 158
<212> TYPE: PRT
<213> ORGANISM: Rhodococcus erythropolis

<400> SEQUENCE: 10

Met Arg Val Gly Leu Gly Thr Asp Val His Pro Ile Glu Val Gly Arg
1               5                   10                  15

Pro Cys Trp Met Ala Gly Leu Leu Phe Glu Glu Ala Asp Gly Cys Ser
            20                  25                  30

Gly His Ser Asp Gly Asp Val Ala Val His Ala Leu Cys Asp Ala Leu
        35                  40                  45

Leu Ser Ala Ala Gly Leu Gly Asp Leu Gly Ser Val Phe Gly Thr Gly
    50                  55                  60
```

```
Arg Pro Glu Trp Asp Gly Val Ser Gly Ala Arg Met Leu Ala Glu Val
 65                  70                  75                  80

Arg Arg Leu Leu Glu Glu Asn Gln Phe Thr Val Gly Asn Ala Ala Val
                 85                  90                  95

Gln Val Ile Gly Asn Arg Pro Lys Ile Gly Pro Arg Arg Asp Glu Ala
            100                 105                 110

Gln Lys Val Leu Ser Asp Ile Leu Gly Ala Pro Val Ser Val Ser Ala
        115                 120                 125

Thr Thr Thr Asp Gly Leu Gly Leu Thr Gly Arg Gly Glu Gly Ile Ala
    130                 135                 140

Ala Met Ala Thr Ala Leu Val Met Thr Thr Glu His Asp Arg
145                 150                 155

<210> SEQ ID NO 11
<211> LENGTH: 1035
<212> TYPE: DNA
<213> ORGANISM: Rhodococcus erythropolis

<400> SEQUENCE: 11
gtgagcaccg aaaagactgc tgccgacgca accgcatcga gcaccgtcgt tgcaggcatc      60
gacctgggcg acgaacagct cgccgcagta gtgcgtggtg gactctccga tgtcgaggag     120
ttgttggtca gcgagctgtc cgacggcgaa gacttcctca ccgaggccgc gctgcatctc     180
gcgcgagccg gggaaagcg cttccgtccg ttgttcacga tcctgaccgc gcaactcgga      240
ccggtgccga acgatccgtc gatcatcacc gcagcgaccg tcaccgaact cgttcacctg     300
gcgacgctct atcacgacga cgtcatggac gaggcctcca tgcggcgcgg agcacccagc     360
gccaacgccc gctggggaaa cagcgtggcg atcctggccg cgactatct gttcgcgcac      420 gcatcacgcc tggtatcgac gctcggaccc gaagctgttc ggatcatcgc cgaaaccttt     480
gcagagctgg tcaccggcca gatgcgcgag acgatcggcg tcaagaagga acaggatccg     540
gtcgagcatt acctcaaggt cgtgtgggag aagaccggtt cgctcatcgc tgcatccgga     600
cgattcggcg gcactttctc cggcgccgac gcagctcaca tcgagcgcct cgagcgcctg     660
ggtgacgccg tcggcaccgc attccagatc tccgacgaca tcatcgacat ctcctccgta     720
tcggcgcagt ccggcaagac tccgggcacc gacctgcgcg aggggtgtcca cacccctgccc    780 gtcctgtacg cgttccgcga agaaggagcc gacgcagatc gcctgcggga gctgctcgcg     840
ggcccggtca ccgaagacgc actggtagaa gaagctctcg aactgctcga gcgttcgccg     900
ggcatggtca aggcgaaggc aaagctgggc gagtacgcag tctcggcaaa ggcccagttg     960
gccgagctcc gcagggacc ggcgaatgaa gcgctcgtgc cctcgtgga ctacacgatc      1020 gaacgagtcg gctga                                                       1035

<210> SEQ ID NO 12
<211> LENGTH: 344
<212> TYPE: PRT
<213> ORGANISM: Rhodococcus erythropolis

<400> SEQUENCE: 12

Met Ser Thr Glu Lys Thr Ala Ala Asp Ala Thr Ala Ser Ser Thr Val
1               5                   10                  15

Val Ala Gly Ile Asp Leu Gly Asp Glu Gln Leu Ala Ala Val Val Arg
            20                  25                  30

Gly Gly Leu Ser Asp Val Glu Glu Leu Leu Val Ser Glu Leu Ser Asp
        35                  40                  45
```

-continued

Gly Glu Asp Phe Leu Thr Glu Ala Ala Leu His Leu Ala Arg Ala Gly
    50                  55                  60

Gly Lys Arg Phe Arg Pro Leu Phe Thr Ile Leu Thr Ala Gln Leu Gly
65                  70                  75                  80

Pro Val Pro Asn Asp Pro Ser Ile Ile Thr Ala Ala Thr Val Thr Glu
                85                  90                  95

Leu Val His Leu Ala Thr Leu Tyr His Asp Asp Val Met Asp Glu Ala
            100                 105                 110

Ser Met Arg Arg Gly Ala Pro Ser Ala Asn Ala Arg Trp Gly Asn Ser
        115                 120                 125

Val Ala Ile Leu Ala Gly Asp Tyr Leu Phe Ala His Ala Ser Arg Leu
    130                 135                 140

Val Ser Thr Leu Gly Pro Glu Ala Val Arg Ile Ala Glu Thr Phe
145                 150                 155                 160

Ala Glu Leu Val Thr Gly Gln Met Arg Glu Thr Ile Gly Val Lys Lys
                165                 170                 175

Glu Gln Asp Pro Val Glu His Tyr Leu Lys Val Val Trp Glu Lys Thr
            180                 185                 190

Gly Ser Leu Ile Ala Ala Ser Gly Arg Phe Gly Gly Thr Phe Ser Gly
        195                 200                 205

Ala Asp Ala Ala His Ile Glu Arg Leu Glu Arg Leu Gly Asp Ala Val
    210                 215                 220

Gly Thr Ala Phe Gln Ile Ser Asp Asp Ile Ile Asp Ile Ser Ser Val
225                 230                 235                 240

Ser Ala Gln Ser Gly Lys Thr Pro Gly Thr Asp Leu Arg Glu Gly Val
                245                 250                 255

His Thr Leu Pro Val Leu Tyr Ala Phe Arg Glu Glu Gly Ala Asp Ala
            260                 265                 270

Asp Arg Leu Arg Glu Leu Leu Ala Gly Pro Val Thr Glu Asp Ala Leu
        275                 280                 285

Val Glu Glu Ala Leu Glu Leu Leu Glu Arg Ser Pro Gly Met Val Lys
    290                 295                 300

Ala Lys Ala Lys Leu Gly Glu Tyr Ala Val Ser Ala Lys Ala Gln Leu
305                 310                 315                 320

Ala Glu Leu Pro Gln Gly Pro Ala Asn Glu Ala Leu Val Arg Leu Val
                325                 330                 335

Asp Tyr Thr Ile Glu Arg Val Gly
            340

<210> SEQ ID NO 13
<211> LENGTH: 1140
<212> TYPE: DNA
<213> ORGANISM: Rhodococcus erythropolis

<400> SEQUENCE: 13
ttggaggcca ccctgtccgc aggaaccgcg cgcgttggac agagttcgac caacaccgca      60
ccgcatccga cctcactcga actgccaggc gtgttcgaag agcgctccg cgacttcttc      120 gattcacgcc gcgaactcgt ctcgaacatc ggcggtggat acgagaaagc cgtcagcacc      180
ctcgaagcct tcgtcctgcg cggaggaaag cgcgtccggc cgtcgttcgc ctggacggga      240
tggctcggcg ccggaggcga cccgaacggg agcggcgcgg acgcggtgat tcgtgcatgc      300
gcggccctcg aactggtgca ggcctgcgcg ctcgtccacg acgacatcat cgacgcatca      360
acgaccaggc gcggcttccc gaccgttcac gtcgaattcg aggaccagca ccgaggcgag      420

-continued

```
gagtggagcg gcgactccgc gcacttcggc gaggccgtcg ccattctcct cggcgacctg      480
gccttggcct gggctgacga catgatccga gaatccggga tcagcccga cgcggccgca       540 cgagtgagcc cggtctggtc ggcaatgcgc accgaggtgc ttggtggcca attcctcgac      600
atcagcaacg aagcccgcgg agacgagacc gtcgaggcag ccatgcgggt caaccgttac     660
aaaaccgccg cgtacacgat cgaacgccca ctgcacctcg cgccgcatt gttcggtgca      720 gacgccgagt tgatcgatgc ctaccggacg ttcggcaccg acatcgggat tgccttccaa     780
cttcgcgacg acctgctcgg tgtcttcgga gatccgtccg tcacgggcaa accgtcgggc    840
gacgatctca tcgccggtaa gcggactgtc ctgttcgcga tggcgcttgc ccgcgccgac   900
gccgcagatc cggcggcagc agaactgctc cgcaacggaa tcggcaccca gttgaccgac   960
aacgaagtcg acactctgcg tcaggtgatc accgatcttg cgccgtcac cgacgtcgaa   1020 acgcagatcg acaccctcgt cgaggcagct gcgaacgccc tcgactcgag cacggcaacg  1080
gcagagtcca aggctcgcct gaccgatatg gcgatcgcgg ccacgaagcg aagctactga   1140
```

<210> SEQ ID NO 14
<211> LENGTH: 378
<212> TYPE: PRT
<213> ORGANISM: Rhodococcus erythropolis

<400> SEQUENCE: 14

```
Met Glu Ala Thr Leu Ser Ala Gly Thr Ala Arg Val Gly Gln Ser Ser
1               5                   10                  15

Thr Asn Thr Ala Pro His Pro Thr Ser Leu Glu Leu Pro Gly Val Phe
                20                  25                  30

Glu Gly Ala Leu Arg Asp Phe Phe Asp Ser Arg Glu Leu Val Ser
            35                  40                  45

Asn Ile Gly Gly Gly Tyr Glu Lys Ala Val Ser Thr Leu Glu Ala Phe
        50                  55                  60

Leu Arg Gly Gly Lys Arg Val Arg Pro Ser Phe Ala Trp Thr Gly Trp
65                  70                  75                  80

Leu Gly Ala Gly Gly Asp Pro Asn Gly Ser Gly Ala Asp Ala Val Ile
                85                  90                  95

Arg Ala Cys Ala Ala Leu Glu Leu Val Gln Ala Cys Ala Leu Val His
            100                 105                 110

Asp Asp Ile Ile Asp Ala Ser Thr Thr Arg Arg Gly Phe Pro Thr Val
        115                 120                 125

His Val Glu Phe Glu Asp Gln His Arg Gly Glu Glu Trp Ser Gly Asp
    130                 135                 140

Ser Ala His Phe Gly Glu Ala Val Ala Ile Leu Leu Gly Asp Leu Ala
145                 150                 155                 160

Leu Ala Trp Ala Asp Asp Met Ile Arg Glu Ser Gly Ile Ser Pro Asp
                165                 170                 175

Ala Ala Ala Arg Val Ser Pro Val Trp Ser Ala Met Arg Thr Glu Val
            180                 185                 190

Leu Gly Gly Gln Phe Leu Asp Ile Ser Asn Glu Ala Arg Gly Asp Glu
        195                 200                 205

Thr Val Glu Ala Ala Met Arg Val Asn Arg Tyr Lys Thr Ala Ala Tyr
    210                 215                 220

Thr Ile Glu Arg Pro Leu His Leu Gly Ala Ala Leu Phe Gly Ala Asp
225                 230                 235                 240

Ala Glu Leu Ile Asp Ala Tyr Arg Thr Phe Gly Thr Asp Ile Gly Ile
```

```
                245                 250                 255
Ala Phe Gln Leu Arg Asp Asp Leu Leu Gly Val Phe Gly Asp Pro Ser
                260                 265                 270

Val Thr Gly Lys Pro Ser Gly Asp Asp Leu Ile Ala Gly Lys Arg Thr
            275                 280                 285

Val Leu Phe Ala Met Ala Leu Ala Arg Ala Asp Ala Ala Asp Pro Ala
        290                 295                 300

Ala Ala Glu Leu Leu Arg Asn Gly Ile Gly Thr Gln Leu Thr Asp Asn
305                 310                 315                 320

Glu Val Asp Thr Leu Arg Gln Val Ile Thr Asp Leu Gly Ala Val Thr
                325                 330                 335

Asp Val Glu Thr Gln Ile Asp Thr Leu Val Glu Ala Ala Ala Asn Ala
            340                 345                 350

Leu Asp Ser Ser Thr Ala Thr Ala Glu Ser Lys Ala Arg Leu Thr Asp
        355                 360                 365

Met Ala Ile Ala Ala Thr Lys Arg Ser Tyr
    370                 375
```

<210> SEQ ID NO 15
<211> LENGTH: 945
<212> TYPE: DNA
<213> ORGANISM: Rhodococcus erythropolis

<400> SEQUENCE: 15

```
atgaacgcat tgtctgcgtc ctatgaattc tgcgaggacg tgacgaggga acacggccga     60
acgtactttc tggccactcg gttgctgccc gagcctcgac gccgcgcagt tcacgctctc    120
tacgcatttg ctcgcgtcgt cgacgacgtc gtggacgaac cctcgggtcc acatgaacga    180
ggcacggtgc tcgccgacgt cgaacgtgca gccgtcaccg cactcgacaa ccccactgcg    240
acaggtggct ccccgtcgac gattcccctc gacctgacac gcgtactccc tgccttcgcc    300
gatgctgtga agacgttcga cattccgcgt gcatacttcg acgccttctt cgagtccatg    360
cggatggacg cccccgacac cgcgaagttt cgacccgtct acaacacgat ggacgagctt    420
gccgagtaca tgtacggctc cgccgtcgtc atcggtttgc agatgctccc gattctcgga    480
gtgagcgttc cgcagcagga agctgtagtg cccgcgtcga atctcggtga ggcgtttcag    540
ctgaccaact tcatccgcga cgtcggtgaa gacctcgacc ggggacgtct gtatctcccg    600
gcgggcgagt cgccgcgatt cggggtcgac atcgagatgc tcgagcacgg cgcagaacc     660
ggaacggtgg acgttcgggt caagcgcgcg ctggcacact tcattgcagt gacgcggggg    720
cggtatcggt ccgccgaatc cggcatcccg atgctcgatc ggcgggtcca gccgtcgatc    780
cgcacggctt tcgtgttgta cggagcaatt ctcgaccagg tcgagcgcgc cgacttccgg    840
atactgcatc gacgagtgtc cgttcccgga cgcacgcgac ttcgagtcgc tgcgccgggt    900
ctggtccggt cggcaaccta cgcggcgaaa accgcatga ggtga                     945
```

<210> SEQ ID NO 16
<211> LENGTH: 314
<212> TYPE: PRT
<213> ORGANISM: Rhodococcus erythropolis

<400> SEQUENCE: 16

```
Met Asn Ala Leu Ser Ala Ser Tyr Glu Phe Cys Glu Asp Val Thr Arg
1               5                   10                  15

Glu His Gly Arg Thr Tyr Phe Leu Ala Thr Arg Leu Leu Pro Glu Pro
            20                  25                  30
```

```
Arg Arg Arg Ala Val His Ala Leu Tyr Ala Phe Ala Arg Val Val Asp
        35                  40                  45

Asp Val Val Asp Glu Pro Ser Gly Pro His Glu Arg Gly Thr Val Leu
 50                  55                  60

Ala Asp Val Glu Arg Ala Ala Val Thr Ala Leu Asp Asn Pro Thr Ala
65                  70                  75                  80

Thr Gly Gly Phe Pro Ser Thr Ile Pro Leu Asp Leu Thr Arg Val Leu
                85                  90                  95

Pro Ala Phe Ala Asp Ala Val Lys Thr Phe Asp Ile Pro Arg Ala Tyr
               100                 105                 110

Phe Asp Ala Phe Phe Glu Ser Met Arg Met Asp Ala Pro Asp Thr Ala
               115                 120                 125

Lys Phe Arg Pro Val Tyr Asn Thr Met Asp Glu Leu Ala Glu Tyr Met
   130                 135                 140

Tyr Gly Ser Ala Val Val Ile Gly Leu Gln Met Leu Pro Ile Leu Gly
145                 150                 155                 160

Val Ser Val Pro Gln Gln Glu Ala Val Val Pro Ala Ser Asn Leu Gly
                165                 170                 175

Glu Ala Phe Gln Leu Thr Asn Phe Ile Arg Asp Val Gly Glu Asp Leu
               180                 185                 190

Asp Arg Gly Arg Leu Tyr Leu Pro Ala Gly Glu Phe Ala Ala Phe Gly
           195                 200                 205

Val Asp Ile Glu Met Leu Glu His Gly Arg Arg Thr Gly Thr Val Asp
210                 215                 220

Val Arg Val Lys Arg Ala Leu Ala His Phe Ile Ala Val Thr Arg Gly
225                 230                 235                 240

Arg Tyr Arg Ser Ala Glu Ser Gly Ile Pro Met Leu Asp Arg Arg Val
                245                 250                 255

Gln Pro Ser Ile Arg Thr Ala Phe Val Leu Tyr Gly Ala Ile Leu Asp
               260                 265                 270

Gln Val Glu Arg Ala Asp Phe Arg Ile Leu His Arg Arg Val Ser Val
   275                 280                 285

Pro Gly Arg Thr Arg Leu Arg Val Ala Ala Pro Gly Leu Val Arg Ser
   290                 295                 300

Ala Thr Tyr Ala Ala Lys Asn Arg Met Arg
305                 310

<210> SEQ ID NO 17
<211> LENGTH: 1593
<212> TYPE: DNA
<213> ORGANISM: Rhodococcus erythropolis

<400> SEQUENCE: 17
gtggcagacg tgcaccgcac tcgaaccgtc agctcgccga ccgatcgagt cgtgatcgtc    60
ggcgcgggac ttgccggact gtctgcgggg ttgtatctgc gtggcgccgg ccgcgacgtc   120
acgatcctcg agagcaacgg ctcggtcggc gggcgagtcg tgtctacca gggcagtgac   180 tacagcatcg acaacggcgc aacggtgctc acgatgcccg aactcgtcga agacgctctt   240
gcggccgtcg cgccgacccc cgactcgaca aaccccaaat tcgttgtgca caagctcgat   300
ccgacgtacc acgcgcgatt cgcagacggc acctctctcg atgttcacgc cgaccccgaa   360
gacatggctg ccgaagtctc tcgtgtctgc gggccggaag aagcgcagcg ataccgtgcg   420
ttgcggcgat ggctgaaccg catcttcgac gcggaattcg accgcttcat ggacgccgac   480
```

-continued

```
ttcgattctc ccctcggact ggtcaattcg cgtgaagcag tcaaggatct gagccgactc    540
gtcgcactgg gaggattcgg gaaactgggc gggcaggtgg atcgcaagat ccgcgaccct    600
cgcctccggc ggatcttcac tttccaagcg ctgtatgcgg agttgctcc gtctcgagcc    660
ctcgcggtgt acgggcgat cgctcacatg gacacctcac tgggcgtcta ctttcccgag    720
ggcgggatgc gcacgatcgc cgagtcgatg gccgacgctt tcaccgaggc cggcggaatt    780
ctgcatctcg gccgcacggt cgaacgactc gaggtgagcg accgtcgcgt gcgtgccgta    840
cacacatgcg acggtgagag cttcgactgt gacgtcgcag tcctcacccc cgacatggcc    900
gtcacggact ccctcttgcg cccgcatacg cgattgcgcc cgcgaccggt gcgtacatcg    960
ccgtccgcgg tcgtgattca cggcactgtt tcttcagccg tcgccgacgg atggcccgcg   1020
cagcgacacc acatgatcga cttcggcgag gcgtggaagc gcaccttcgc cgagatcacg   1080
gcacgccgcg ccgcgggca attgatgagt gatccgtcac tgctcgtcac ccgaccggcg   1140
cagaccgacc cgagcctggc cttctcgcga cacggccgga tccgtgaacc gctgtcagtc   1200
ctcgcgccgt gcccgaatct ggacagtgcg ccgctcgact gggcagttct cggcccggcc   1260
tacgtgcgtg aaatcatcct cacgctgcaa gaacgtggct atacgggact ggtcgagggg   1320
ttcgatatcg atcacgtcga caccccgcag acctggctcg agaagggcat ggccgcgggt   1380
agcccgttcg cggcggcaca caccttcacc cagacggggc cgttccgacg caagaacctc   1440
gccccgcggct tcgacaacgt cgttctcgcc ggatcgggaa ccgttccggg ggtgggagta   1500
ccgaccgttc tgctgtccgg ccggctcgcc gccgaacgta ttaccggtac acgcgagcga   1560
gccagcgcgg tgggcactcg tgcgagcaac taa                                1593
```

<210> SEQ ID NO 18
<211> LENGTH: 530
<212> TYPE: PRT
<213> ORGANISM: Rhodococcus erythropolis

<400> SEQUENCE: 18

```
Met Ala Asp Val His Arg Thr Arg Thr Val Ser Ser Pro Thr Asp Arg
1               5                   10                  15

Val Val Ile Val Gly Ala Gly Leu Ala Gly Leu Ser Ala Gly Leu Tyr
            20                  25                  30

Leu Arg Gly Ala Gly Arg Asp Val Thr Ile Leu Glu Ser Asn Gly Ser
        35                  40                  45

Val Gly Gly Arg Val Gly Val Tyr Gln Gly Ser Asp Tyr Ser Ile Asp
    50                  55                  60

Asn Gly Ala Thr Val Leu Thr Met Pro Glu Leu Val Glu Asp Ala Leu
65                  70                  75                  80

Ala Ala Val Gly Ala Asp Pro Asp Ser Thr Asn Pro Lys Phe Val Val
                85                  90                  95

His Lys Leu Asp Pro Thr Tyr His Ala Arg Phe Ala Asp Gly Thr Ser
            100                 105                 110

Leu Asp Val His Ala Asp Pro Glu Asp Met Ala Ala Glu Val Ser Arg
        115                 120                 125

Val Cys Gly Pro Glu Glu Ala Gln Arg Tyr Arg Ala Leu Arg Arg Trp
    130                 135                 140

Leu Asn Arg Ile Phe Asp Ala Glu Phe Asp Arg Phe Met Asp Ala Asp
145                 150                 155                 160

Phe Asp Ser Pro Leu Gly Leu Val Asn Ser Arg Glu Ala Val Lys Asp
                165                 170                 175
```

-continued

```
Leu Ser Arg Leu Val Ala Leu Gly Gly Phe Gly Lys Leu Gly Gly Gln
                180                 185                 190

Val Asp Arg Lys Ile Arg Asp Pro Arg Leu Arg Arg Ile Phe Thr Phe
            195                 200                 205

Gln Ala Leu Tyr Ala Gly Val Ala Pro Ser Arg Ala Leu Ala Val Tyr
        210                 215                 220

Gly Ala Ile Ala His Met Asp Thr Ser Leu Gly Val Tyr Phe Pro Glu
225                 230                 235                 240

Gly Gly Met Arg Thr Ile Ala Glu Ser Met Ala Asp Ala Phe Thr Glu
                245                 250                 255

Ala Gly Gly Ile Leu His Leu Gly Arg Thr Val Glu Arg Leu Glu Val
            260                 265                 270

Ser Asp Arg Arg Val Arg Ala Val His Thr Cys Asp Gly Glu Ser Phe
        275                 280                 285

Asp Cys Asp Val Ala Val Leu Thr Pro Asp Met Ala Val Thr Asp Ser
290                 295                 300

Leu Leu Arg Pro His Thr Arg Leu Arg Pro Arg Pro Val Arg Thr Ser
305                 310                 315                 320

Pro Ser Ala Val Val Ile His Gly Thr Val Ser Ser Ala Val Ala Asp
                325                 330                 335

Gly Trp Pro Ala Gln Arg His His Met Ile Asp Phe Gly Glu Ala Trp
            340                 345                 350

Lys Arg Thr Phe Ala Glu Ile Thr Ala Arg Arg Gly Arg Gly Gln Leu
        355                 360                 365

Met Ser Asp Pro Ser Leu Leu Val Thr Arg Pro Ala Gln Thr Asp Pro
370                 375                 380

Ser Leu Ala Phe Ser Arg Asp Gly Arg Ile Arg Glu Pro Leu Ser Val
385                 390                 395                 400

Leu Ala Pro Cys Pro Asn Leu Asp Ser Ala Pro Leu Asp Trp Ala Val
                405                 410                 415

Leu Gly Pro Ala Tyr Val Arg Glu Ile Ile Leu Thr Leu Gln Glu Arg
            420                 425                 430

Gly Tyr Thr Gly Leu Val Glu Gly Phe Asp Ile Asp His Val Asp Thr
        435                 440                 445

Pro Gln Thr Trp Leu Glu Lys Gly Met Ala Ala Gly Ser Pro Phe Ala
        450                 455                 460

Ala Ala His Thr Phe Thr Gln Thr Gly Pro Phe Arg Arg Lys Asn Leu
465                 470                 475                 480

Ala Arg Gly Phe Asp Asn Val Val Leu Ala Gly Ser Gly Thr Val Pro
                485                 490                 495

Gly Val Gly Val Pro Thr Val Leu Leu Ser Gly Arg Leu Ala Ala Glu
            500                 505                 510

Arg Ile Thr Gly Thr Arg Glu Arg Ala Ser Ala Val Gly Thr Arg Ala
        515                 520                 525

Ser Asn
    530
```

<210> SEQ ID NO 19
<211> LENGTH: 1131
<212> TYPE: DNA
<213> ORGANISM: Rhodococcus erythropolis

<400> SEQUENCE: 19
atgagcacac tcgactcctc cgccgacgtg gtgatcgtgg gcggagggcc ggcggggcgg         60

```
gcactcgcga cgcgctgtat cgcccggcaa ctcactgttg tcgttgtcga tccgcatcct    120
catcgggtgt ggacgccgac gtactcggtg tgggcagaca gctgccgtc gtggctgccg     180 gacgaggtga tcgcgagccg aatcgaacgc ccgagcgtgt ggaccagcgg gcagaaaacg    240
cttgatcgca tctattgcgt attgaataca tctttactgc aatcatttct ctcccacaca    300
tccataaagg tcagaggctt acgcgctcaa acactgtcca ccaccaccgt cgtgtgcgtg    360
gacggatcgc agctgacggg atccgtcgtc gtcgacgccc gaggcaccga tctggcagtg    420
acaaccgcgc agcagacggc cttcggaatg atcgtggacc gagctctggc cgatccgatt    480
ctgggcggca gcgaggcctg gttcatggac tggcgaacag acaacggcac ctccgacgcc    540
gacactccgt cgtttctcta cgcggtcccg ctcgacgacg agcgagtcct cctcgaggag    600
acctgcctcg tcggccggcc ggcgttgggg ttgcgtgaac tcgaaacacg tctgcgcacc    660
cgacttcaca atcggggctg cgaagtcccc gacgacgcgc cggtcgagcg agtccgtttt    720
gcggtcgaag gcccgaggga ctcgtccccg gacggtgtcc tccggttcgg cgggcgaggc    780
ggtctgatgc atccgggaac cggatacagc gttgcctcct cactcgccga ggccgacact    840
gtcgcgaaag caatcgccga cggtgaggat ccgaacgcgg cactctggcc tcgctcggcc    900
aaggcggtat ccgctctccg ccgcgttggt ctgaacgcac ttctcaccct cgactcgggc    960
gaagtcacca cattcttcga caagttcttc gatctaccgg tcgaggctca gcggtcatac    1020
ctttccgatc ggcgggacgc ggccgcgacg gcgaaggtga tggcaacact gttccgatcg    1080
tcaccgtggc acgtcagaaa gacgttgatg cgcgcgccgt ttttccggtg a             1131
```

<210> SEQ ID NO 20
<211> LENGTH: 376
<212> TYPE: PRT
<213> ORGANISM: Rhodococcus erythropolis

<400> SEQUENCE: 20

```
Met Ser Thr Leu Asp Ser Ala Asp Val Val Ile Val Gly Gly Gly
1               5                   10                  15

Pro Ala Gly Arg Ala Leu Ala Thr Arg Cys Ile Ala Arg Gln Leu Thr
            20                  25                  30

Val Val Val Asp Pro His Pro His Arg Val Trp Thr Pro Thr Tyr
        35                  40                  45

Ser Val Trp Ala Asp Glu Leu Pro Ser Trp Leu Pro Asp Glu Val Ile
    50                  55                  60

Ala Ser Arg Ile Glu Arg Pro Ser Val Trp Thr Ser Gly Gln Lys Thr
65                  70                  75                  80

Leu Asp Arg Ile Tyr Cys Val Leu Asn Thr Ser Leu Leu Gln Ser Phe
                85                  90                  95

Leu Ser His Thr Ser Ile Lys Val Arg Gly Leu Arg Ala Gln Thr Leu
            100                 105                 110

Ser Thr Thr Thr Val Val Cys Val Asp Gly Ser Gln Leu Thr Gly Ser
        115                 120                 125

Val Val Val Asp Ala Arg Gly Thr Asp Leu Ala Val Thr Thr Ala Gln
    130                 135                 140

Gln Thr Ala Phe Gly Met Ile Val Asp Arg Ala Leu Ala Asp Pro Ile
145                 150                 155                 160

Leu Gly Gly Ser Glu Ala Trp Phe Met Asp Trp Arg Thr Asp Asn Gly
                165                 170                 175

Thr Ser Asp Ala Asp Thr Pro Ser Phe Leu Tyr Ala Val Pro Leu Asp
            180                 185                 190
```

Asp Glu Arg Val Leu Leu Glu Glu Thr Cys Leu Val Gly Arg Pro Ala
        195                 200                 205

Leu Gly Leu Arg Glu Leu Glu Thr Arg Leu Arg Thr Arg Leu His Asn
    210                 215                 220

Arg Gly Cys Glu Val Pro Asp Asp Ala Pro Val Glu Arg Val Arg Phe
225                 230                 235                 240

Ala Val Glu Gly Pro Arg Asp Ser Ser Pro Asp Gly Val Leu Arg Phe
                245                 250                 255

Gly Gly Arg Gly Gly Leu Met His Pro Gly Thr Gly Tyr Ser Val Ala
                260                 265                 270

Ser Ser Leu Ala Glu Ala Asp Thr Val Ala Lys Ala Ile Ala Asp Gly
        275                 280                 285

Glu Asp Pro Asn Ala Ala Leu Trp Pro Arg Ser Ala Lys Ala Val Ser
    290                 295                 300

Ala Leu Arg Arg Val Gly Leu Asn Ala Leu Leu Thr Leu Asp Ser Gly
305                 310                 315                 320

Glu Val Thr Thr Phe Phe Asp Lys Phe Phe Asp Leu Pro Val Glu Ala
                325                 330                 335

Gln Arg Ser Tyr Leu Ser Asp Arg Arg Asp Ala Ala Thr Ala Lys
                340                 345                 350

Val Met Ala Thr Leu Phe Arg Ser Ser Pro Trp His Val Arg Lys Thr
    355                 360                 365

Leu Met Arg Ala Pro Phe Phe Arg
    370                 375

<210> SEQ ID NO 21
<211> LENGTH: 19
<212> TYPE: DNA
<213> ORGANISM: artificial sequence
<220> FEATURE:
<223> OTHER INFORMATION: primer

<400> SEQUENCE: 21
gagtttgatc ctggctcag                                                19

<210> SEQ ID NO 22
<211> LENGTH: 16
<212> TYPE: DNA
<213> ORGANISM: artificial sequence
<220> FEATURE:
<223> OTHER INFORMATION: primer

<400> SEQUENCE: 22
taccttgtta cgactt                                                    16

<210> SEQ ID NO 23
<211> LENGTH: 17
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (11)..(11)
<223> OTHER INFORMATION: Y = C or T
<220> FEATURE:
<221> NAME/KEY: misc_feature
<222> LOCATION: (12)..(12)
<223> OTHER INFORMATION: M = A or C

<400> SEQUENCE: 23

```
gtgccagcag ymgcggt                                                  17

<210> SEQ ID NO 24
<211> LENGTH: 20
<212> TYPE: DNA
<213> ORGANISM: artificial sequence
<220> FEATURE:
<223> OTHER INFORMATION: primer

<400> SEQUENCE: 24
atttcgttga acggctcgcc                                               20

<210> SEQ ID NO 25
<211> LENGTH: 20
<212> TYPE: DNA
<213> ORGANISM: artificial sequence
<220> FEATURE:
<223> OTHER INFORMATION: primer

<400> SEQUENCE: 25
cggcaatccg acctctacca                                               20

<210> SEQ ID NO 26
<211> LENGTH: 20
<212> TYPE: DNA
<213> ORGANISM: artificial sequence
<220> FEATURE:
<223> OTHER INFORMATION: primer

<400> SEQUENCE: 26
tgagacgagc cgtcagcctt                                               20

<210> SEQ ID NO 27
<211> LENGTH: 29
<212> TYPE: DNA
<213> ORGANISM: artificial sequence
<220> FEATURE:
<223> OTHER INFORMATION: primer

<400> SEQUENCE: 27
catgccatgg cctcgaagcc ttcgtcctg                                     29

<210> SEQ ID NO 28
<211> LENGTH: 30
<212> TYPE: DNA
<213> ORGANISM: artificial sequence
<220> FEATURE:
<223> OTHER INFORMATION: primer

<400> SEQUENCE: 28
catgccatgg cgcagagtgt cgacttcgtt                                    30

<210> SEQ ID NO 29
<211> LENGTH: 32
<212> TYPE: DNA
<213> ORGANISM: artificial sequence
<220> FEATURE:
<223> OTHER INFORMATION: primer

<400> SEQUENCE: 29
ttcatgccat ggactcgtcg aagacgctct tg                                 32

<210> SEQ ID NO 30
<211> LENGTH: 30
<212> TYPE: DNA
<213> ORGANISM: artificial sequence
```

```
<220> FEATURE:
<223> OTHER INFORMATION: primer

<400> SEQUENCE: 30
ttcatgccat ggtgacgagc agtgacggat                                          30

<210> SEQ ID NO 31
<211> LENGTH: 18
<212> TYPE: DNA
<213> ORGANISM: artificial sequence
<220> FEATURE:
<223> OTHER INFORMATION: primer

<400> SEQUENCE: 31
agcggcatca gcaccttg                                                       18

<210> SEQ ID NO 32
<211> LENGTH: 21
<212> TYPE: DNA
<213> ORGANISM: artificial sequence
<220> FEATURE:
<223> OTHER INFORMATION: primer

<400> SEQUENCE: 32
gccaatatgg acaacttctt c                                                   21

<210> SEQ ID NO 33
<211> LENGTH: 24
<212> TYPE: DNA
<213> ORGANISM: artificial sequence
<220> FEATURE:
<223> OTHER INFORMATION: primer

<400> SEQUENCE: 33
atccgacctc actcgaactg ccag                                                24

<210> SEQ ID NO 34
<211> LENGTH: 24
<212> TYPE: DNA
<213> ORGANISM: artificial sequence
<220> FEATURE:
<223> OTHER INFORMATION: primer

<400> SEQUENCE: 34
ggtcggcgag ctgacggttc gagt                                                24

<210> SEQ ID NO 35
<211> LENGTH: 24
<212> TYPE: DNA
<213> ORGANISM: artificial sequence
<220> FEATURE:
<223> OTHER INFORMATION: primer

<400> SEQUENCE: 35
cggccacgaa gcgaagctac tgac                                                24

<210> SEQ ID NO 36
<211> LENGTH: 24
<212> TYPE: DNA
<213> ORGANISM: artificial sequence
<220> FEATURE:
<223> OTHER INFORMATION: primer

<400> SEQUENCE: 36
atcgtggatg aatggtcggt tacg                                                24
```